(12) United States Patent
Jung et al.

(10) Patent No.: US 12,070,360 B2
(45) Date of Patent: Aug. 27, 2024

(54) METHOD OF SHARING INFORMATION IN ULTRASOUND IMAGING

(71) Applicant: SAMSUNG ELECTRONICS CO., LTD., Suwon-si (KR)

(72) Inventors: Jongwoo Jung, Hwaseong-si (KR); Eun-ho Yang, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1460 days.

(21) Appl. No.: 16/031,669

(22) Filed: Jul. 10, 2018

(65) Prior Publication Data

US 2018/0317890 A1 Nov. 8, 2018

Related U.S. Application Data

(63) Continuation of application No. 14/320,971, filed on Jul. 1, 2014, now abandoned.

(30) Foreign Application Priority Data

Jul. 1, 2013 (KR) .................. 10-2013-0076594
Jun. 25, 2014 (KR) .................. 10-2014-0078390

(51) Int. Cl.
*A61B 8/00* (2006.01)
*A61B 8/08* (2006.01)
(Continued)

(52) U.S. Cl.
CPC ............... *A61B 8/565* (2013.01); *A61B 8/13* (2013.01); *A61B 8/465* (2013.01); *A61B 8/468* (2013.01);
(Continued)

(58) Field of Classification Search
CPC ............ A61B 8/565; A61B 8/13; A61B 8/465; A61B 8/468; A61B 8/469; A61B 8/52; G16H 30/20; G16H 30/40
See application file for complete search history.

(56) References Cited

U.S. PATENT DOCUMENTS 5,715,823 A 2/1998 Wood et al.
5,938,607 A 8/1999 Jago et al.
(Continued)

FOREIGN PATENT DOCUMENTS

CN 200963151 Y 10/2007
CN 101371792 A 2/2009
(Continued)

OTHER PUBLICATIONS

Communication dated Jul. 20, 2021, from the China National Intellectual Property Administration in Application No. 201480048196.X.

(Continued)

*Primary Examiner* — Joseph M Santos Rodriguez
*Assistant Examiner* — Amy Shafqat
(74) *Attorney, Agent, or Firm* — Sughrue Mion, PLLC

(57) ABSTRACT

An ultrasound apparatus includes a probe to acquire ultrasound data from an object; a communicator; a display; and a processor to generate a first ultrasound image based on the ultrasound data; display the first ultrasound image on the display; control the communicator to transmit the first ultrasound image to an external device so that the first ultrasound image is displayed on the external device; generate a second ultrasound image based on the ultrasound data and a control command received from the external device, the control command being based on a touch input with respect to the first ultrasound image displayed on the external device; display the second ultrasound image on the (Continued)

display; and control the communicator to transmit the second ultrasound image to the external device so that the second ultrasound image is displayed on the external device.

20 Claims, 26 Drawing Sheets

(51) Int. Cl.
  *A61B 8/13* (2006.01)
  *G16H 30/20* (2018.01)
  *G16H 30/40* (2018.01)

(52) U.S. Cl.
  CPC ............ *A61B 8/469* (2013.01); *G16H 30/20* (2018.01); *G16H 30/40* (2018.01); *A61B 8/52* (2013.01)

(56) References Cited

U.S. PATENT DOCUMENTS

| | | | |
|---|---|---|---|
| 6,210,327 | B1 | 4/2001 | Brackett et al. |
| 6,475,146 | B1 | 11/2002 | Frelburger et al. |
| 6,500,122 | B1* | 12/2002 | Washburn ........... G01S 7/52073 600/443 |
| 8,334,867 | B1* | 12/2012 | Davidson ............ G06F 3/04845 715/848 |
| 8,972,847 | B2 | 3/2015 | Jin et al. |
| 9,301,000 | B2 | 3/2016 | Kim et al. |
| 9,561,015 | B2 | 2/2017 | Halmann et al. |
| 10,524,739 | B2 | 1/2020 | Roncalez et al. |
| 2002/0173721 | A1 | 11/2002 | Grunwald et al. |
| 2004/0204649 | A1 | 10/2004 | Ramraj et al. |
| 2005/0043620 | A1 | 2/2005 | Fallows et al. |
| 2005/0203389 | A1 | 9/2005 | Williams |
| 2006/0149597 | A1* | 7/2006 | Powell ................... G16H 10/60 600/300 |
| 2006/0173346 | A1 | 8/2006 | Lee |
| 2008/0039722 | A1 | 2/2008 | Mejia et al. |
| 2009/0054777 | A1 | 2/2009 | Amemiya et al. |
| 2009/0177453 | A1 | 7/2009 | Kouchi et al. |
| 2010/0055656 | A1 | 3/2010 | Lemme |
| 2010/0179427 | A1* | 7/2010 | Yamamoto ............. A61B 8/469 600/443 |
| 2010/0251109 | A1 | 9/2010 | Jin et al. |
| 2012/0157844 | A1* | 6/2012 | Halmann ............. A61B 8/0841 600/443 |
| 2012/0311088 | A1 | 12/2012 | Heere et al. |
| 2013/0123603 | A1 | 5/2013 | Shin |
| 2014/0275851 | A1 | 9/2014 | Amble et al. |

FOREIGN PATENT DOCUMENTS

| | | |
|---|---|---|
| CN | 101933039 A | 12/2010 |
| CN | 101959463 A | 1/2011 |
| CN | 102579077 A | 7/2012 |
| JP | 2004-041594 A | 2/2004 |
| JP | 2005-110739 A | 4/2005 |
| JP | 2005-110974 A | 4/2005 |
| JP | 2008-173174 A | 7/2008 |
| JP | 2008-293171 A | 12/2008 |
| JP | 2012-231228 A | 11/2012 |
| KR | 10-1998-0024940 A | 7/1998 |
| KR | 10-0319912 B1 | 4/2002 |
| KR | 10-2010-0107684 A | 10/2010 |
| KR | 10-1093050 B1 | 12/2011 |
| KR | 10-2012-0055763 A | 6/2012 |
| KR | 10-2013-53587 A | 5/2013 |

OTHER PUBLICATIONS

Communication dated Mar. 22, 2021 issued by the State Intellectual Property Office of P.R. China in counterpart Chinese Application No. 201810811083.0.
Communication issued Nov. 12, 2019 by the State Intellectual Property Office of P.R. China in counterpart Chinese Patent Application No. 201480048196.X.
Communication dated Dec. 2, 2014 issued by the European Patent Office in counterpart European Patent Application No. 14175277.4.
International Search Report for PCT/KR2014/005705 dated Sep. 12, 2014 [PCT/ISA/210].
Written Opinion for PCT/KR2014/005705 dated Sep. 12, 2014 [PCT/ISA/237].
Koutelakis et al., ("Application of Multiprotocol Medical Imaging Communications and an Extended Dicom Wado Service in a Teleradiology Architecture", International Journal of Telemedicine and Applications. vol. 2012, Jun. 13, 2011).
Communication dated Jun. 28, 2019 issued by the State Intellectual Property Office of P.R. China in counterpart Chinese Application No. 201480048196.X.
Chinese Office Action dated Feb. 2, 2019 issued by the State Intellectual Property Office of P.R. China in counterpart Chinese Application No. 201480048196.X.
Communication dated May 8, 2020 issued by the Korean Intellectual Property Office in counterpart Korean Application No. 10-2014-0078390.
Communication dated Nov. 12, 2020, issued by the Korean Intellectual Property Office in corresponding Korean Application No. 10-2014-0078390.
Communication dated Mar. 14, 2022 issued by the European Patent Office in European Patent Application No. 21213125.4.
Communication dated Jan. 18, 2024, issued by the European Patent Office in corresponding European Patent Application No. 21213125.4.

* cited by examiner

METHOD OF SHARING INFORMATION IN ULTRASOUND IMAGING

CROSS-REFERENCE TO RELATED PATENT APPLICATIONS

This is a continuation of U.S. application Ser. No. 14/320,971 filed Jul. 1, 2014, which claims priority from Korean Patent Application No. 10-2013-0076594, filed on Jul. 1, 2013, in the Korean Intellectual Property Office, and from Korean Patent Application No. 10-2014-0078390, filed on Jun. 25, 2014, in the Korean Intellectual Property Office, the disclosures of which are incorporated herein in their entireties by reference.

BACKGROUND

1. Field

Apparatuses and methods consistent with exemplary embodiments relate to sharing information about ultrasound images between an ultrasound apparatus and an external device.

2. Description of the Related Art

An ultrasound diagnostic apparatus transfers ultrasound signals from a surface of an object toward a predetermined portion inside the object to obtain a tomogram image of a soft tissue or an image about blood flow by using information of the ultrasound signal reflected from the internal regions of the object.

An ultrasound diagnostic apparatus is small, inexpensive, and has high reliability without a risk of X-ray exposure, and, thus, is widely used in addition to other imaging diagnostic apparatuses such as an X-ray diagnostic apparatus, a computed tomography (CT) scanner, a magnetic resonance imaging (MRI) apparatus, and a nuclear medicine imaging apparatus.

However, there may be a large time difference between a point of time when a medical technician captures an ultrasound image and a point of time when a doctor analyzes the corresponding ultrasound image. Therefore, it takes a long time to diagnose the ultrasound image, and, often, an ultrasound image needs to be captured again. Thus, the medical professionals and patients may experience inconvenience. Accordingly, there is a need for an ultrasound diagnostic system allowing to quickly identify and review an ultrasound image when a medical technician captures the ultrasound image.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide an ultrasound apparatus sharing ultrasound information about an ultrasound image with a receiving device according to a sharing level of the receiving device, and an information sharing method of the ultrasound apparatus.

One or more exemplary embodiments also provide a medical expert device capable of sending and receiving information about an ultrasound image to and from an ultrasound apparatus, and a communication method of the medical expert device.

According to an aspect of an exemplary embodiment, there is provided a method of sharing information with an external device by an ultrasound apparatus, the method including: acquiring an ultrasound image of an object by transmitting an ultrasound signal to the object and receiving an ultrasound response signal from the object; identifying a sharing level of an external device, which is set in advance, for sharing the ultrasound image; and transmitting ultrasound information about the ultrasound image to the external device according to the sharing level that is set in advance.

The ultrasound information may be displayed on the external device in real-time.

The external device may include a first device and a second device, and the transmitting may include: transmitting first ultrasound information corresponding to a first sharing level of the first device to the first device; and transmitting second ultrasound information corresponding to a second sharing level of the second device to the second device.

The first device may include a patient device, and the second device may include a medical expert device.

The transmitting of the ultrasound information may include generating the ultrasound information by adding at least one annotation related to all or some of the ultrasound image to the ultrasound image.

The adding of the at least one annotation to the ultrasound image may include: analyzing the ultrasound image; recommending at least one annotation related to all or some of the ultrasound image based on a result of the analyzing; and displaying the at least one recommended annotation on the ultrasound image.

The adding of the at least one annotation to the ultrasound image may include: displaying an annotation list that is set in advance; receiving a selection of at least one annotation from the annotation list; and displaying the selected at least one annotation on the ultrasound image.

The displaying of the selected at least one annotation on the ultrasound image may include: receiving a drag and drop input that includes dragging the selected at least one annotation to a region where the ultrasound image is displayed and dropping the at least one annotation; and displaying the selected at least one annotation on the ultrasound image based on the drag and drop input.

The method may further include: when a touch input of touching the at least one annotation displayed on the ultrasound image for a predetermined length of time or longer is received, activating the touched annotation to be moved; receiving a drag input of the user on the touched at least one annotation; and moving the touched at least one annotation according to the drag input of the user.

The method may further include: providing an activated annotation list about at least one annotation added to the ultrasound image on a predetermined region of a screen.

The transmitting of the ultrasound information may include: selecting a region of interest from the ultrasound image; indicating an identification mark on the region of interest; and transmitting the ultrasound information including information about the region of interest that is indicated by the identification mark to the external device.

The indicating of the identification mark may include: adding a color to the region of interest.

The transmitting of the second ultrasound information may include generating the second ultrasound information including at least one of analysis information about the ultrasound image, by the ultrasound technician, measurement information with respect to the ultrasound image, and patient information.

The method may further include: receiving a message about the ultrasound image from the external device; and displaying the received message on a screen.

The method may further include: providing a chatting window for communicating with the medical expert device on a screen; receiving a user input about the ultrasound image through the chatting window; transmitting the user input to the medical expert device; and receiving a response message to the user input from the medical expert device.

The method may further include: transmitting a request for confirmation about the second ultrasound information to the medical expert device; and receiving a confirmation message of the second ultrasound information from the medical expert device.

The method may further include: receiving control information from the medical expert device; and executing a control command corresponding to the control information.

The control information may include at least one of a control command for selecting and displaying another ultrasound image, a control command for expanding or reducing the ultrasound image, a control command for storing the ultrasound image, a control command for three-dimensional (3D) rendering the ultrasound image, a control command for adding an annotation or a body marker, a control command for measuring the region of interest, and a control command for correcting the analysis information about the ultrasound image.

The method may further include: providing a list of devices that are capable of communicating with the ultrasound apparatus; and receiving a selection of the external device from the list of devices.

The method may further include: requesting a server for an authentication of the selected external device; and receiving information of a sharing level of the external device from the server, when the authentication has succeeded.

According to another aspect of an exemplary embodiment, there is provided a method of communicating with at least one ultrasound apparatus by a medical expert device, the method including: displaying an ultrasound image list including at least one ultrasound image acquired by the at least one ultrasound apparatus on a first region of a screen; receiving a selection of an ultrasound image from the ultrasound image list; displaying the selected ultrasound image on a second region of the screen; and communicating with an ultrasound apparatus that acquires the selected ultrasound image.

The displaying of the ultrasound image list may include displaying the ultrasound list including a real-time ultrasound image transmitted from the at least one ultrasound apparatus and an ultrasound image stored in advance.

The displaying of the ultrasound image list may further include indicating an identification mark on the real-time ultrasound image to distinguish the real-time ultrasound image from the ultrasound image stored in advance.

The displaying of the selected ultrasound image may include displaying at least one of analysis information by an ultrasound technician about the selected ultrasound image, measurement information with respect to the selected ultrasound image, and patient information, according to a sharing level of the medical expert device.

The displaying of the selected ultrasound image may include displaying a pointer of the ultrasound apparatus and a pointer of the medical expert device on the selected ultrasound image.

The communicating may include: providing a chatting window for communicating with the ultrasound apparatus on a third region of the screen; receiving an input about the selected ultrasound image through the chatting window; and transmitting the received input to the ultrasound apparatus.

The communicating may include: receiving a request for confirmation about the selected ultrasound image from the ultrasound apparatus; receiving confirmation information about the selected ultrasound image; and transmitting the confirmation information to the ultrasound apparatus.

The transmitting of the confirmation information may include: displaying a graphical user interface (GUI) for receiving a confirmation input of the selected ultrasound image; and receiving a confirmation input about the selected ultrasound image through the GUI.

The communicating may include transmitting control information for controlling the ultrasound apparatus to the ultrasound apparatus.

The transmitting of the control information may include transmitting to the ultrasound apparatus at least one of a control command for selecting and displaying another ultrasound image, a control command for expanding or reducing the ultrasound image, a control command for storing the ultrasound image, a control command for 3D rendering the ultrasound image, a control command for adding an annotation or a body marker, a control command for measuring the region of interest, and a control command for correcting the analysis information about the ultrasound image.

The method may further include communicating with a patient device that displays the selected ultrasound image.

The communicating with the patient device may include: receiving a description by a medical expert about the selected ultrasound image; and transmitting the description by the medical expert to the patient device.

The description by the medical expert may be displayed on the patient device in real-time.

According to another aspect of an exemplary embodiment, there is provided a method of communicating with a patient device by a medical expert device, the method including: displaying an ultrasound image of a patient on a screen of the medical expert device; receiving a description by a medical expert about the ultrasound image; and transmitting the description by the medical expert to the patient device displaying the ultrasound image, wherein the description by the medical expert is displayed on the patient device.

The description by the medical expert may be displayed on the patient device in real-time, or stored in the patient device.

According to another aspect of an exemplary embodiment, there is provided an ultrasound apparatus including: an ultrasound image obtainer for acquiring an ultrasound image of an object by transmitting an ultrasound signal to the object and receiving an ultrasound response signal from the object; a controller for identifying a sharing level of an external device, which is set in advance, for sharing the ultrasound image; and a communicator for transmitting ultrasound information about the ultrasound image to the external device, according to the sharing level that is set in advance.

The external device may include a first device and a second device, and the controller generates first ultrasound information corresponding to a first sharing level of the first device, and second ultrasound information corresponding to a second sharing level of the second device.

The ultrasound apparatus may further include an image processor for adding at least one annotation relating to all or some of the ultrasound image to the ultrasound image.

The ultrasound apparatus may further include: a user input unit for receiving a selection of at least one annotation from the annotation list displayed on the screen; and a display for displaying the selected at least one annotation on the ultrasound image.

The user input unit may receive a drag and drop input that includes dragging the selected at least one annotation to a region where the ultrasound image is displayed and dropping the at least one annotation, and the display may display the selected at least one annotation on the ultrasound image based on the drag and drop input.

When a touch input of touching the annotation displayed on the ultrasound image for a predetermined length of time or longer is received, the controller may activate the touched at least one annotation to be moved, the user input unit receives a drag input of the user on the touched at least one annotation, and the display may move the touched at least one annotation according to the drag input of the user The ultrasound apparatus may further include a display for providing an activated annotation list about at least one annotation added to the ultrasound image on a predetermined region of the screen.

The controller may generate the ultrasound information by selecting a region of interest from the ultrasound image and adding a color to the region of interest.

The second ultrasound information may include at least one of analysis information by an ultrasound technician about the ultrasound image, measurement information with respect to the ultrasound apparatus, and patient information.

The communicator may receive a message about the ultrasound image from the external device, and the controller may control the display to display the received message on a screen.

The ultrasound apparatus may further include: a display for providing a chatting window for communicating with the second device on a screen; and a user input unit for receiving a user input about the ultrasound image through the chatting window, wherein the communicator may transmit the user input to the second device and receive a response message to the user input from the second device.

The communicator may transmit a request for confirmation about the second ultrasound information to the second device and receive a confirmation message of the second ultrasound information from the second device.

The communicator may receive control information from the medical expert device, and the controller may execute a control command corresponding to the control information.

The ultrasound apparatus may further include: a display for providing a list of devices that are capable of communicating with the ultrasound apparatus; and a user input unit for receiving a selection of the external device from the list of devices.

The communicator may request a server for an authentication of the selected external device, and receive information of a sharing level of the external device from the server, when the authentication has succeeded.

According to another aspect of an exemplary embodiment, there is provided a medical expert device including: a display for displaying an ultrasound image list including at least one ultrasound image acquired by at least one ultrasound apparatus on a first region of a screen, and displaying a ultrasound image selected from the ultrasound image list on a second region of the screen; a user input unit for receiving a selection of the ultrasound image from the ultrasound image list; a communicator for communicating with an ultrasound apparatus that acquires the selected ultrasound image; and a controller for controlling the display, the user input unit, and the communicator.

The ultrasound image list may include a real-time ultrasound image transmitted from the at least one ultrasound apparatus and an ultrasound image stored in advance.

The controller may indicate an identification mark on the real-time ultrasound image to distinguish the real-time ultrasound image from the ultrasound image stored in advance.

The display may display at least one of analysis information by an ultrasound technician about the selected ultrasound image, measurement information with respect to the selected ultrasound image, and patient information, according to a sharing level of the medical expert device.

The display may display a pointer of the ultrasound apparatus and a pointer of the medical expert device on the selected ultrasound image.

The display may provide a chatting window for communicating with the ultrasound apparatus on a third region of the screen, the user input unit may receive an input about the selected ultrasound image through the chatting window, and the communicator may transmit the received input to the ultrasound apparatus.

The communicator may receive a request for confirmation about the selected ultrasound image from the ultrasound apparatus, and transmit the confirmation information to the ultrasound apparatus.

The display may display a graphical user interface (GUI) for receiving a confirmation input of the selected ultrasound image, and receive a confirmation input about the selected ultrasound image through the GUI.

The communicator may transmit control information for controlling the ultrasound apparatus to the ultrasound apparatus.

The user input unit may receive a description by a medical expert about the selected ultrasound image, and the communicator may transmit the description by the medical expert to the patient device.

According to another aspect of an exemplary embodiment, there is provided a method of sharing information in a medical imaging apparatus, the method including: acquiring a medical image of an object; selecting an external device for sharing information about the medical image; identifying a sharing level of the external device that is selected; and transmitting the information about the medical image to the external device based on the sharing level.

The sharing level may include information representing an authority of a user of the external device for checking the information about the medical image.

The external device may include a first device and a second device, and the transmitting of the information may include: transmitting first medical image information corresponding to a first sharing level of the first device to the first device; and transmitting second medical image information corresponding to a second sharing level of the second device to the second device.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
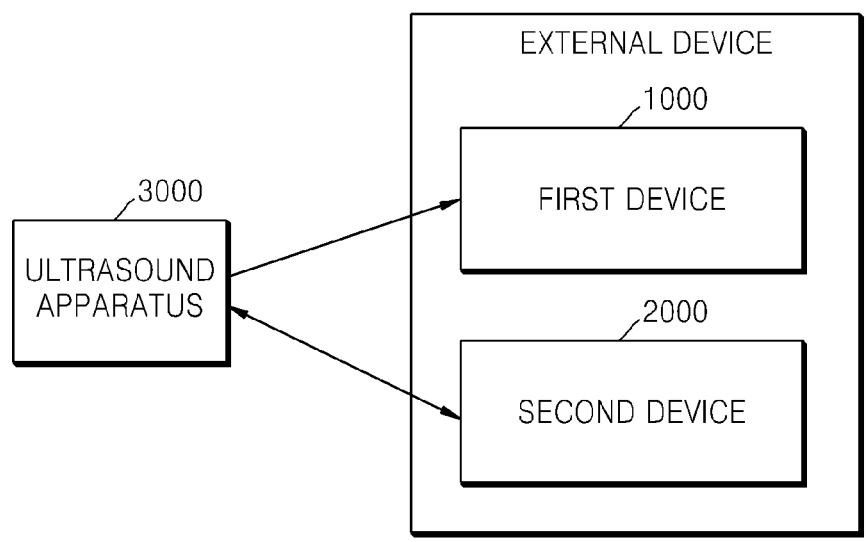
FIG. 1 is a block diagram of an information sharing system according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

General and widely-used terms are used herein, in consideration of provided functions, and may vary according to an intention of one of ordinary skill in the art, a precedent, or emergence of new technologies. Additionally, in some cases, an applicant may arbitrarily select specific terms, in which case, the applicant will provide the meaning of the terms in the description. Accordingly, it will be understood that the terms used herein should be interpreted as having a meaning that is consistent with their meaning in the context of the relevant art and will not be interpreted in an idealized or overly formal sense unless expressly so defined herein.

It will be further understood that the terms "comprises," "comprising," "includes," and/or "including," when used herein, specify the presence of components, but do not preclude the presence or addition of one or more other components, unless otherwise specified. Additionally, terms used herein, such as 'unit' or 'module', mean entities for processing at least one function or operation. These entities may be implemented by hardware, software, or a combination of hardware and software. Expressions such as "at least one of," when preceding a list of elements, modify the entire list of elements and do not modify the individual elements of the list. As used herein, the term "and/or" includes any and all combinations of one or more of the associated listed items.

In the present specification, 'ultrasound image' is an image of an object acquired by using ultrasound signals. The object may denote a human or a body part. For example, the object may include an organ such as a liver, heart, brain, breast, and abdomen, or a fetus, or nuchal translucency (NT).

The ultrasound image may be at least one of a brightness mode (B mode) image representing a magnitude of an ultrasound echo signal reflected by an object as brightness, a color mode (C mode) image representing a velocity of a moving object as a color by using a Doppler effect, a Doppler mode (D mode) image representing an object of a moving object as a spectrum by using a Doppler effect, a motion mode (M mode) image representing movement of an object at a constant location according to time, and an elastic mode image representing a difference between reactions when a compression is applied and not applied to an object as an image; however, an exemplary embodiment is not limited thereto. According to exemplary embodiments, the ultrasound image may be a two-dimensional (2D) image, a 3D image, or a four-dimensional (4D) image.

FIG. 1 is a block diagram of an information sharing system according to an exemplary embodiment.

The information sharing system according to an exemplary embodiment may include an ultrasound apparatus 3000 and an external device (for example, at least one of a first device 1000 and a second device 2000).

According to an exemplary embodiment, the first device 1000 may be a display apparatus for providing an ultrasound image. For example, the first device 1000 may be a device for a patient, i.e., a patient device, which displays an ultrasound image to view by the patient, an authorized family member, an authorized friend, etc.

The first device 1000 may receive ultrasound information about an ultrasound image from the ultrasound apparatus 3000. The first device 1000 may receive the ultrasound information directly from the ultrasound apparatus 3000, or via a server.

The ultrasound device received by the first device 1000 may be ultrasound information corresponding to a sharing level (i.e., authority) of the first device 1000. For example, the ultrasound information corresponding to the sharing level of the first device 1000 may include ultrasound image information, caption (or annotation) information for illustrating all or part of the ultrasound image, and identification mark information for identifying a region of interest (ROI) in the ultrasound image; however, an exemplary embodiment is not limited thereto.

The sharing level of the first device 1000 may be set by an information sharing system or an authorized user, in advance.

The second device 2000 may be a device of a medical expert, which may perform a data communication with the ultrasound apparatus 3000, i.e., a medical expert device. In the present specification, a medical expert may be an expert who can analyze or confirm an ultrasound image transmitted from the ultrasound apparatus 3000 by using the second device 2000. For example, the medical expert may include a doctor, a technician, a medical technologist, a nurse, or a radiologist; however, an exemplary embodiment is not limited thereto.

The medical expert according to an exemplary embodiment may be different from a technician who acquires an ultrasound image by using the ultrasound apparatus 3000. For example, if a first technician acquires an ultrasound image of an object by using the ultrasound apparatus 3000, a second technician or a doctor may identify the ultrasound image acquired by the first technician or analysis information generated by the first technician by using the second device 2000.

The second device 2000 according to an exemplary embodiment may receive ultrasound information about the ultrasound image from the ultrasound apparatus 3000, and may display the ultrasound information on a screen thereof. The second device 2000 may receive the ultrasound information corresponding to a sharing level (i.e., authority) of the second device 2000.

According to an exemplary embodiment, the second device 2000 and the first device 1000 may have sharing levels different from each other. Therefore, the ultrasound information corresponding to the sharing level of the second device 2000 may be different from ultrasound information corresponding to the sharing level of the first device 1000.

For example, the ultrasound information corresponding to the sharing level of the second device 2000 may include analysis information generated by the technician, information about a patient, and measurement information; however, an exemplary embodiment is not limited thereto.

The second device 2000 according to an exemplary embodiment may be a device having an authority to control the ultrasound apparatus 3000 remotely. That is, the second device 2000 may transmit control information for controlling the ultrasound apparatus 3000 based on an input of the medical expert (for example, a doctor).

For example, the second device 2000 may transmit to the ultrasound apparatus 300 a control command for selecting and displaying another ultrasound image, a control command for expanding or reducing the ultrasound image, a control command for storing the ultrasound image, a control command for performing a 3D rendering of the ultrasound image, a control command for adding an annotation or a body marker, a control command for measuring a region of interest, and a control command for correcting analysis information about the ultrasound image.

The ultrasound apparatus 3000 of an exemplary embodiment is a device that acquires ultrasound image data of an object by using ultrasound waves and shares ultrasound information about the ultrasound image with an external device.

The ultrasound apparatus 3000 of an exemplary embodiment may include a mobile terminal or a stationary terminal. Examples of the mobile terminal may include a laptop computer, a personal digital assistant (PDA), a tablet personal computer (PC), and a smartphone.

The ultrasound apparatus 3000 of an exemplary embodiment may transmit the ultrasound information to a receiving device (for example, the first device 1000 or the second device 2000) according to the sharing level of the receiving device. That is, the ultrasound apparatus 3000 may determine a type and/or amount of pieces of information to be transmitted to the receiving device, according to the sharing level of the receiving device.

For example, the ultrasound apparatus 3000 may transmit different ultrasound information to the patient display device and the medical expert display device. When performing the ultrasound diagnosis, there is no need to expose a lot of information to the patient, and thus, an amount of ultrasound information transferred to the patient display device may be less than that of ultrasound information transferred to the medical expert display device. Also, an annotation or a color may be added to the ultrasound information that is transmitted to the patient display apparatus.

The ultrasound apparatus 3000 of an exemplary embodiment may transmit the ultrasound information in various ways. For example, the ultrasound apparatus 3000 may encode ultrasound information about an ultrasound image by using a mirroring technology using a miracast, and may transmit the encoded ultrasound information to the first device 1000 or the second device 2000 via Wi-Fi Direct (WFD). An encoding algorithm according to an exemplary embodiment may include MPEG-2, MPEG-4, H.264, or advanced video coding (AVC); however, exemplary embodiments are not limited thereto.

The ultrasound apparatus 3000 may transmit the ultrasound information to the first device 1000 or the second device 2000 via wireless fidelity (Wi-Fi), Bluetooth, ultra wideband (UWB), or IEEE 1394 communication, but exemplary embodiments are not limited thereto.

The ultrasound apparatus 3000 according to an exemplary embodiment may include a touch screen. The touch screen may be configured to detect a touch input location, a touched area, and a touch input pressure. The touch screen may detect a proximity touch, as well as a real-touch input.

In the present specification, the real-touch input denotes a case where the screen is actually touched by a touch tool (for example, a finger, an electronic pen, etc.), and the proximity touch input denotes a case where a touch tool approaches the screen to within a predetermined distance without actually touching the screen.

The ultrasound apparatus 3000 may sense a touch gesture of a user on an ultrasound image via the touch screen.

Touch gestures of a user may include a tap, a touch and hold, a double tap, a drag, panning, a flick, a drag and drop, a swipe, a pinch, etc.

"Tap" is an operation in which the user touches the screen by using a finger or an electronic pen and then lifts the finger or the electronic pen from the screen without moving it on the screen.

"Touch and hold" is an operation in which the user touches the screen by using a finger or an electronic pen and maintains the touch input for a length of time (for example, two seconds) or longer. That is, a time difference between a touch-in time and a touch-out time is equal to or greater than the length of time (for example, two seconds). In order for the user to recognize whether the touch input is the tap operation or the touch and hold operation, a visual, an audible, or a tactile feedback signal is transmitted when the touch input is maintained for the critical length of time or longer. The length of time may vary.

"Double tap" is an operation in which the user touches the screen twice by using the finger or the electronic pen.

"Drag" is an operation in which the user touches the screen by using a finger or an electronic pen and then moves the finger or the electronic pen to another position on the screen while continuously touching the screen. An object is moved or a panning operation that will be described below is performed by the drag operation.

"Panning" is an operation in which the user performs the drag operation without selecting an object. Since the user does not select a certain object in the panning operation, a page itself moves in the screen or a group of objects moves in the page, without moving the certain object in the page.

"Flick" is an operation in which the user drags a finger or an electronic pen at a certain speed (for example, 100 pixel/s) or faster. The drag operation (or panning operation) and the flick operation may be distinguished from each other based on whether the velocity of the finger or the electronic pen is the certain speed (for example, 100 pixel/s) or greater.

"Drag and drop" is an operation in which the user drags and drops an object at a location on the screen by using the finger or the electronic pen.

"Pinch" is an operation in which the user touches the screen by using two fingers and then moves the fingers to different directions from each other. The pinch operation is a gesture for expanding (pinch open) or reducing (pinch close) the object or the page, and an expansion value or a reduction value may be determined by a distance between two fingers.

"Swipe" is an operation in which the user moves the finger or the electronic pen a distance in a horizontal or a vertical direction in a state of touching the object on the screen. Movement in a diagonal direction is not considered as a swipe event.

The ultrasound apparatus 3000 of an exemplary embodiment may provide some or all of buttons included in a control panel of a general ultrasound apparatus through the touch screen as a graphical user interface (GUI).

Figure 2:
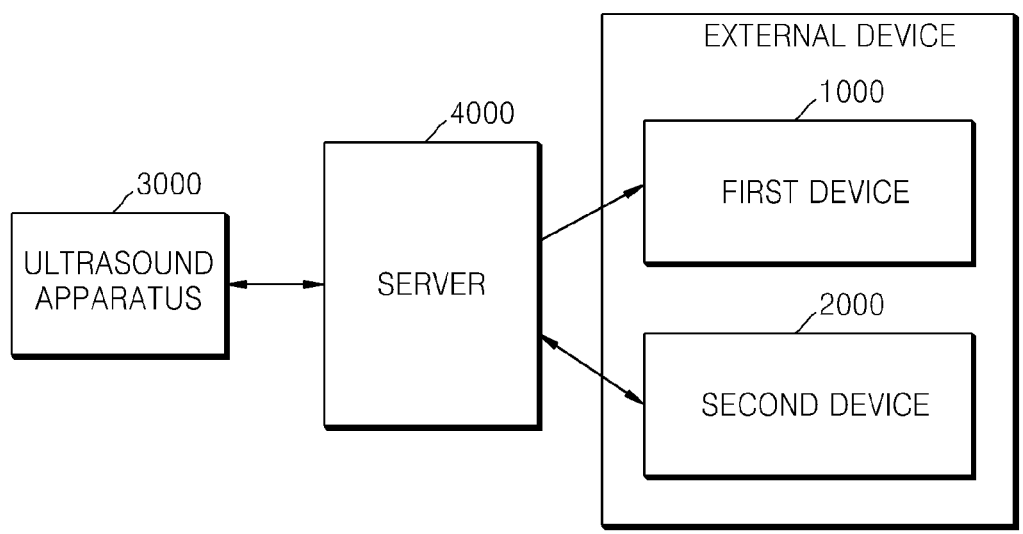
FIG. 2 is a block diagram of an information sharing system according to another exemplary embodiment.

FIG. 2 is a block diagram of an information sharing system according to another exemplary embodiment.

The information sharing system according to an exemplary embodiment may further include a server 4000.

The server 4000 may be a server for managing information related to ultrasound images. The server 4000 according to an exemplary embodiment may include a server of a medical institution (for example, a hospital).

The server 4000 of an exemplary embodiment may store information about patients, and may store information relating to ultrasound images captured by the ultrasound apparatus 3000. The server 4000 may store information about sharing levels of devices that may share information with the ultrasound apparatus 3000. For example, information such as identification information of a device (for example, a device ID, a Mac address, and an equipment name, etc.), the sharing level, types of information that may be shared, and an amount of data that may be shared may be stored in the server 4000 in a table format.

The server 4000 of an exemplary embodiment may transmit information about real-time ultrasound images received from the ultrasound apparatus 3000 to the first device 1000 or the second device 2000. The real-time ultrasound image may refer to an ultrasound image that is captured by the ultrasound apparatus 3000 within a predetermined time period (for example, within five minutes) from the present or at a time of receiving the ultrasound image.

The server 4000 according to an exemplary embodiment may receive a request to transmit a certain ultrasound image that is stored in advance from the second device 2000, and may transmit the requested ultrasound image to the second device 2000.

Hereinafter, a method of sharing ultrasound information about ultrasound images by the ultrasound apparatus 3000 with a plurality of other devices according to a sharing level will be described in more detail with reference to FIG. 3.

Figure 3:
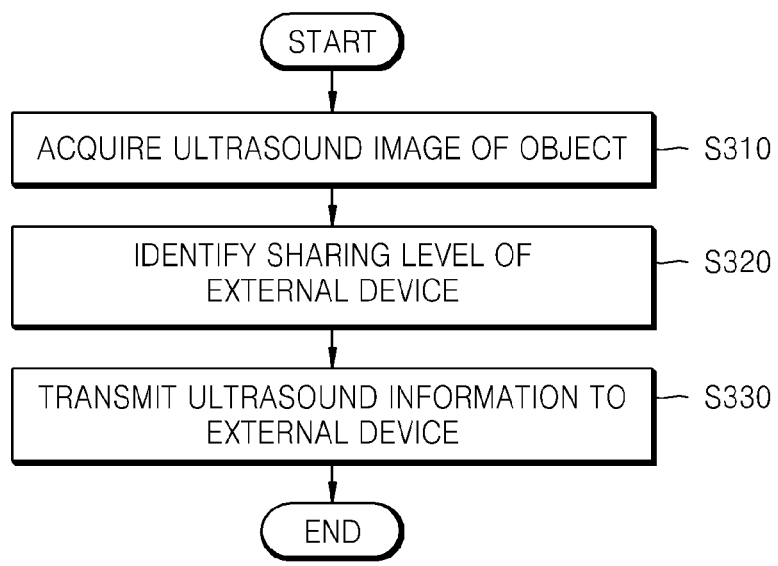
FIG. 3 is a flowchart illustrating an information sharing method, according to an exemplary embodiment.

FIG. 3 is a flowchart illustrating an information sharing method of an ultrasound apparatus 3000, according to an exemplary embodiment.

In operation S310, the ultrasound apparatus 3000 may acquire an ultrasound image about an object. The ultrasound apparatus 3000 of an exemplary embodiment may directly generate the ultrasound image, or may receive the ultrasound image from outside.

For example, the ultrasound apparatus 3000 transmits an ultrasound signal to the object and receives an ultrasound response signal from the object to generate the ultrasound image. Otherwise, the ultrasound apparatus 3000 may receive an ultrasound image from an external server or an external device.

In operation S320, the ultrasound apparatus 3000 may identify a sharing level of an external device for sharing the ultrasound image. For example, the ultrasound apparatus 3000 may identify information about a first sharing level corresponding to identification information of the first device 1000 and/or a second sharing level corresponding to identification information of the second device 2000.

According to an exemplary embodiment, the ultrasound apparatus 3000 may receive information about the first sharing level and/or information about the second sharing level from the server 4000. According to another exemplary embodiment, the ultrasound apparatus 3000 may read the information about the first sharing level and/or the information about the second sharing level from a memory.

According to an exemplary embodiment, the first sharing level of the first device 1000 and the second sharing level of the second device 2000 may be different from each other. For example, if the first device 1000 is the patient device and the second device 2000 is the medical expert device, the sharing level of the first device 1000 may be lower than the sharing level of the second device 2000. The lower sharing level denotes that a number of types and/or amounts of the sharable information are relatively small.

In operation S330, the ultrasound apparatus 3000 may transmit ultrasound information to the external device according to the sharing level. That is, the ultrasound apparatus 3000 may transmit first ultrasound information corresponding to the first sharing level to the first device 1000, or may transmit second ultrasound information corresponding to the second sharing level to the second device 2000.

For example, if the first device 1000 is the patient device and the second device 2000 is the medical expert device, the ultrasound apparatus 3000 shares the ultrasound image only with the first device 1000, and may share additional information in addition to the ultrasound image with the second device 2000. The additional information may include analysis information of a technician, measurement information, and patient information; however, the exemplary embodiment is not limited thereto.

According to an exemplary embodiment, the external device (for example, the first device 1000 and/or the second device 2000) may display the ultrasound information transmitted from the ultrasound apparatus 3000 in real-time. The displaying of the ultrasound information in real-time may denote displaying of the ultrasound information on the screen within a predetermined time period (for example, one minute) from a point of time when the ultrasound information is received. For example, the first device 1000 may display first ultrasound information and the second device 2000 may display second ultrasound information in real-time. For example, the first ultrasound information and the second ultrasound information may include at least the ultrasound image, which has been scanned by the technician, and the patient and the medical expert may share the ultrasound image in real-time.

According to an exemplary embodiment, the ultrasound apparatus 3000 may encode the first ultrasound information by using an encoding code that is negotiated in advance or an encoding code that is set in advance for securing the first ultrasound information, and may transmit the encoded first ultrasound information to the first device 1000. The ultrasound apparatus 3000 encodes the second ultrasound information by using an encoding code that is negotiated in advance or an encoding code that is set in advance for securing the second ultrasound information, and may transmit the encoded second ultrasound information to the second device 2000.

Hereinafter, the method of sharing the ultrasound information by the ultrasound apparatus 3000 according to the sharing level will be described in more detail with reference to FIGS. 4 through 13. For convenience of description, it is assumed that the first device 1000 is a patient device and the second device 2000 is a medical expert device.

Figure 4:
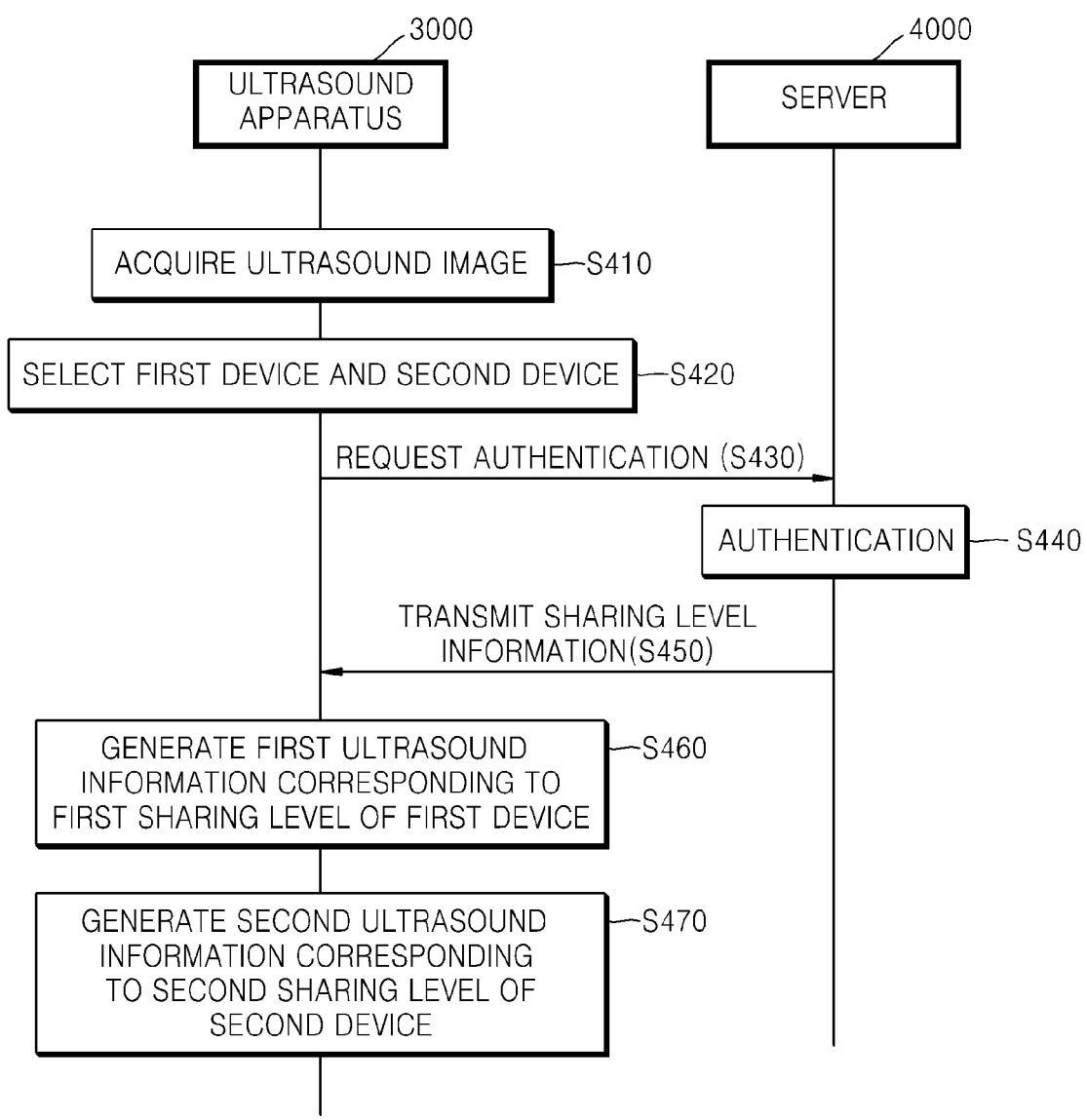
FIG. 4 is a flowchart illustrating a method of generating ultrasound information, according to an exemplary embodiment.

FIG. 4 is a flowchart illustrating a method of generating ultrasound information, according to an exemplary embodiment.

In operation S410, the ultrasound apparatus 3000 may acquire an ultrasound image of an object. For example, the ultrasound apparatus 3000 may acquire a B mode image, a C mode image, a D mode image, an M mode image, an elastic mode image, a 2D ultrasound image, a 3D ultrasound image, and a 4D ultrasound image of the object; however, an exemplary embodiment is not limited thereto. Since operation S410 corresponds to operation S310 shown in FIG. 3, detailed descriptions thereof will not be provided here.

In operation S420, the ultrasound apparatus 3000 may select the first device 1000 and the second device 2000 with which the information will be shared. According to an exemplary embodiment, the ultrasound apparatus 3000 may select the first device 1000 and the second device 2000 connected to the ultrasound apparatus 3000 based on system settings.

According to another exemplary embodiment, the ultrasound apparatus 3000 may select the first device 1000 and the second device 2000 based on a user input. For example, the ultrasound apparatus 3000 may provide a device list including identification information of the devices that may communicate with the ultrasound apparatus 3000 on a screen. The ultrasound apparatus 3000 may receive the user input for selecting the first device 1000 and the second device 2000 in the device list. The user of the ultrasound apparatus 3000 of an exemplary embodiment may be a technician, a medical professional, or an ordinary person; however, the exemplary embodiment is not limited thereto. Hereinafter, the technician will be assumed as the user of the ultrasound apparatus 3000.

In operation S430, the ultrasound apparatus 3000 may request authentication regarding the first device 1000 and the second device 2000 to the server 4000. In operation S440, the server 4000 may perform authentication operations regarding the first device 1000 and the second device 2000. For example, the server 4000 may verify whether each of the first device 1000 and the second device 2000 is a device that may share the information with the ultrasound apparatus 3000. Through the authentication, exposure of the ultrasound information relating to personal medical diagnosis to unspecified public may be prevented.

In operation S450, when the authentication of the first device 1000 and the second device 2000 has succeeded, the server 4000 may transmit the information about the sharing information of the first device 1000 and the second device 2000 to the ultrasound apparatus 3000. That is, the ultrasound apparatus 3000 may receive information about the first sharing level of the first device 1000 and the information about the second sharing level of the second device 2000.

In operation S460, the ultrasound apparatus 3000 may generate the first ultrasound information corresponding to the first sharing level of the first device 1000. For example, when the first device 1000 is the patient device, the ultrasound apparatus 3000 may generate the first ultrasound information including an ultrasound image, annotation for describing the ultrasound image, an identification mark on a region of interest, and measurement information according to the sharing level of the patient device.

The annotation of an exemplary embodiment may include an annotation representing the object (for example, a head of an embryo, liver, heart, carotid, etc.), and an annotation describing a type of the ultrasound image (for example, a Doppler image, an M mode image, an elastic mode image, etc.); however, the exemplary embodiments are not limited thereto.

The identification mark on the region of interest according to an exemplary embodiment may include adding of a color to the region of interest (for example, adding of skin color to the embryo image), adding of a boundary to the region of interest, and adding of a pattern to the region of interest; however, the exemplary embodiments are not limited thereto.

The measurement information according to an exemplary embodiment may include information obtained from measuring the region of interest. For example, the measurement information may include a head girth and a neck girth of an embryo, a head size, a tumor size, etc.; however, the exemplary embodiments are not limited thereto.

In operation S470, the ultrasound apparatus 3000 may generate the second ultrasound information corresponding to the second sharing level of the second device 2000. For example, when the second device 2000 is a medical expert device, the ultrasound apparatus 3000 generates the second ultrasound information including an ultrasound image, measurement information about the ultrasound image, analysis information of the technician about the ultrasound image, and patient information according to the sharing level of the medical expert device.

The measurement information provided to the medical expert device may include more detailed information than that provided to the patient device. For example, the measurement information provided to the medical expert device may include a maximum speed in a sample volume, an inclination in an M mode image, etc., in addition to the head girth and a neck girth of the embryo, head size, and tumor size, etc.

The analysis information of the technician according to an exemplary embodiment may include a result report generated by the technician after performing an ultrasound examination. The patient information of an exemplary embodiment may include a medical history of the patient, heath state information of the patient, body features of the patient, and image history of the patient; however, the exemplary embodiments are not limited thereto.

Therefore, according to an exemplary embodiment, the ultrasound apparatus 3000 may transmit different pieces of the ultrasound information about one ultrasound image respectively to the patient device and the medical expert device according to the sharing level.

According to exemplary embodiments, an order of performing operations S410 to S470 may be changed, and some of the operations may be omitted.

Hereinafter, the first ultrasound information shared by the ultrasound apparatus 3000 with the first device 1000 will be described in detail with reference to FIGS. 5 through 9. The patient device will be described as an example of the first device 1000.

Figure 5:
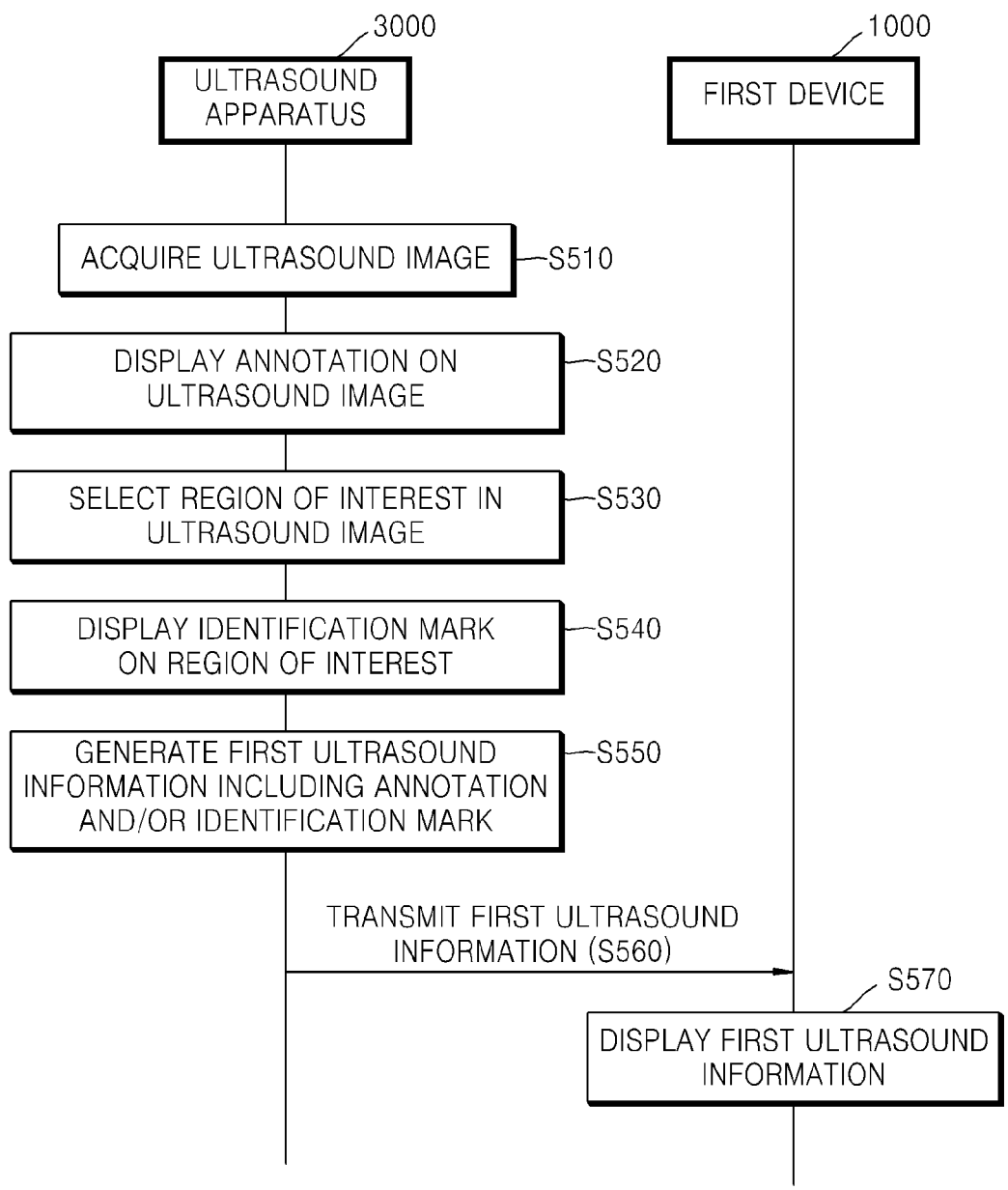
FIG. 5 is a flowchart illustrating a method of generating ultrasound information corresponding to a sharing level of a device, according to an exemplary embodiment.

FIG. 5 is a flowchart illustrating a method of generating the first ultrasound information by the ultrasound apparatus 3000 to correspond to the sharing level of the first device 1000, according to an exemplary embodiment.

In operation S510, the ultrasound apparatus 3000 may acquire an ultrasound image of an object. Since operation S510 corresponds to operation S310 shown in FIG. 3, detailed descriptions thereof will be omitted here.

In operation S520, the ultrasound apparatus 3000 may add at least one annotation to the ultrasound image relating to all or a portion of the ultrasound image.

According to an exemplary embodiment, the ultrasound apparatus 3000 may analyze the ultrasound image to recommend at least one annotation. The ultrasound apparatus 3000 may add at least one annotation to the ultrasound image based on a selection of the user (for example, the technician). For example, the ultrasound apparatus 3000 may display an annotation list that is set in advance. The ultrasound apparatus 3000 receives the user's selection of at least one annotation in the annotation list, and then, may display the selected annotation on the ultrasound image. The adding of the annotation by the ultrasound apparatus 3000 will be described below with reference to FIG. 6.

In operation S530, the ultrasound apparatus 3000 may select a region of interest in the ultrasound image. According to an exemplary embodiment, the ultrasound apparatus 3000 may select the region of interest automatically by analyzing the ultrasound image, or based on the user input.

For example, the ultrasound apparatus 3000 may detect an edge from the ultrasound image and recommend the region of interest automatically. Otherwise, the ultrasound apparatus 3000 may display a graphical user interface (GUI) allowing the user to set the region of interest directly on the screen.

In operation S540, the ultrasound apparatus 3000 may display an identification mark on the region of interest. For example, the ultrasound apparatus 3000 may add a color or a pattern in the region of interest, or may change a thickness of a boundary on the region of interest. This will be described in more detail with reference to FIGS. 7 and 8.

In operation S550, the ultrasound apparatus 3000 may generate first ultrasound information including at least one of the annotation and the identification mark on the region of interest. For example, the ultrasound apparatus 3000 may generate the first ultrasound information including an ultrasound image, to which an annotation for the patient's comprehension is added. The ultrasound apparatus 3000 may generate the first ultrasound information in which the color or the pattern is added to the region of interest, or the first ultrasound information including the annotation and the region of interest on which the identification mark is displayed.

In operation S560, the ultrasound apparatus 3000 may transmit the first ultrasound information to the first device 1000. According to an exemplary embodiment, the ultrasound apparatus 3000 may transmit the first ultrasound information to the first device 1000 via short distance communication. The short distance communication may be Wireless Local Area Network (WLAN) (e.g., Wireless Fidelity (Wi-Fi)), Bluetooth, Bluetooth Low Energy (BLE), UWB, ZigBee, and WFD; however, the exemplary embodiments are not limited thereto.

In operation S570, the first device 1000 receives the first ultrasound information from the ultrasound apparatus 3000, and may display the received first ultrasound information on a screen. The patient may identify the first ultrasound information relating to the ultrasound image acquired by the ultrasound apparatus 3000 via the first device 1000.

According to the exemplary embodiments, an order of performing operations S510 to S570 may be changed, and some operations may be omitted.

Hereinafter, the GUI for generating the first ultrasound information will be described in more detail with reference to FIGS. 6 through 8.

Figure 6:
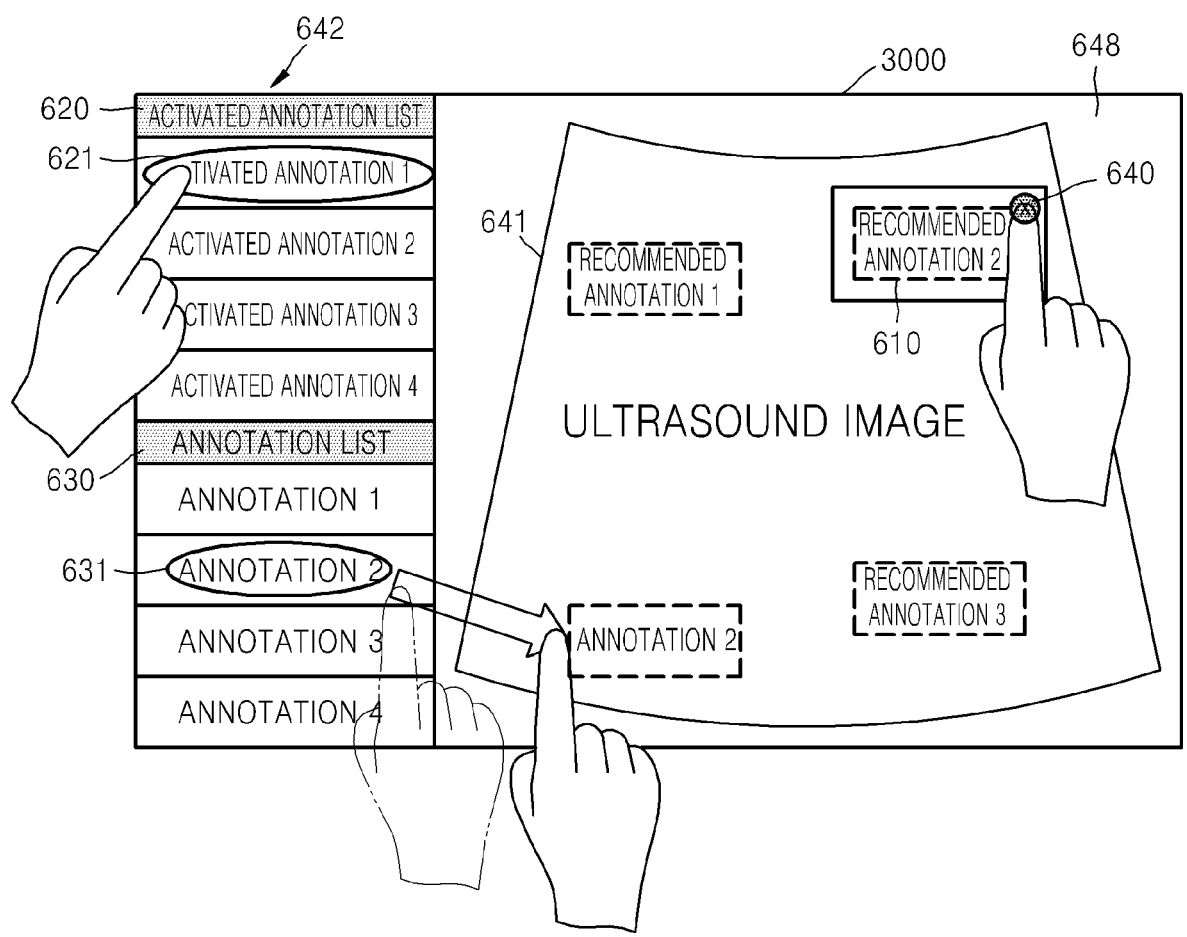
FIG. 6 is a diagram showing a graphical user interface (GUI) for adding an annotation, according to an exemplary embodiment.

FIG. 6 is a diagram showing a GUI for adding an annotation, according to an exemplary embodiment.

The ultrasound apparatus 3000 analyses the information about the ultrasound image to recommend annotations for describing a part or all of the ultrasound image 641 (for example, a recommended annotation 1, a recommended annotation 2, and a recommended annotation 3). For example, the ultrasound apparatus 3000 may analyze the information about the ultrasound image, and may display a recommended annotation for describing the object or a recommended annotation for representing a location of an embryo head at corresponding locations. A method of analyzing the ultrasound image by the ultrasound apparatus 3000 is known to those skilled in the art, and thus, detailed descriptions thereof will not be provided here.

According to an exemplary embodiment, the ultrasound apparatus 3000 may move, delete, or edit a recommended annotation 610 based on a user input. For example, when a touch input for touching the recommended annotation 610 for a predetermined time or longer is received, the ultrasound apparatus 3000 may display a delete icon 640 for deleting the recommended annotation 610. In this case, the user may select the delete icon 640 for deleting the recommended annotation 610.

Also, when the touch input for touching the recommended annotation 610 is maintained for a predetermined length of time or longer, the ultrasound apparatus 3000 may enable the recommended annotation 610 to move. The user may drag the recommended annotation 610 to change the display location of the recommended annotation 610.

According to an exemplary embodiment, the ultrasound apparatus 3000 may provide an annotation list 630 that is set in advance on a predetermined region 642 of the screen for the user's selection. The annotation list 630 of an exemplary embodiment may be displayed on a region that is different from the region 648 where the ultrasound image is displayed.

According to an exemplary embodiment, the annotation included in the annotation list 630 may be arranged based on usage times. For example, the annotations in the annotation list 630 may be arranged in an order from most frequently used by the user.

The annotation list 630 of an exemplary embodiment may include annotations relating to the current ultrasound mode and set in advance, or annotations relating to the target or to the object and set in advance. For example, if the target is an embryo, annotations relating to the embryo may be included in the annotation list 630. The annotation list 630 of an exemplary embodiment may include annotations relating to the identification information of the technician or identification information of the patient.

The ultrasound apparatus 3000 of an exemplary embodiment may receive a selection of the user (for example, the technician) on at least one annotation from the annotation list 630 and may display the selected annotation on the ultrasound image.

For example, the ultrasound apparatus 3000 may sense a drag and drop input which involves dragging a second annotation 631 from the annotation list 630 to the region where the ultrasound image is displayed and dropping the second annotation 631 onto a certain location. The ultrasound apparatus 3000 may display the second annotation 631 at the certain point where the drop input is sensed, based on the drag and drop input.

According to an exemplary embodiment, the ultrasound apparatus 3000 may provide an activated annotation list 620 including identification information of the annotations displayed on the ultrasound image on a predetermined region of the screen. The activated annotation may denote an annotation that is currently displayed on the ultrasound image. For example, the recommended annotation 1, the recommended annotation 2, the recommended annotation 3, and the second annotation 631 displayed on the ultrasound image 641 may be activated annotations. The user may identify the annotations that are added to the current ultrasound image via the activated annotation list 620.

According to an exemplary embodiment, the ultrasound apparatus 3000 may receive a user input for selecting at least one activated annotation from the activated annotation list 620. The ultrasound apparatus 3000 may activate an edit mode of the selected activated annotation.

For example, the user may touch an activated annotation 621 from the activated annotation list 620 for a predetermined time, tap the activated annotation 621, or double-tap the activated annotation 621. Then, the ultrasound apparatus 3000 may activate an edit mode of the activated annotation 621, and may correct the activated annotation 621 displayed on the ultrasound image.

Figure 7:
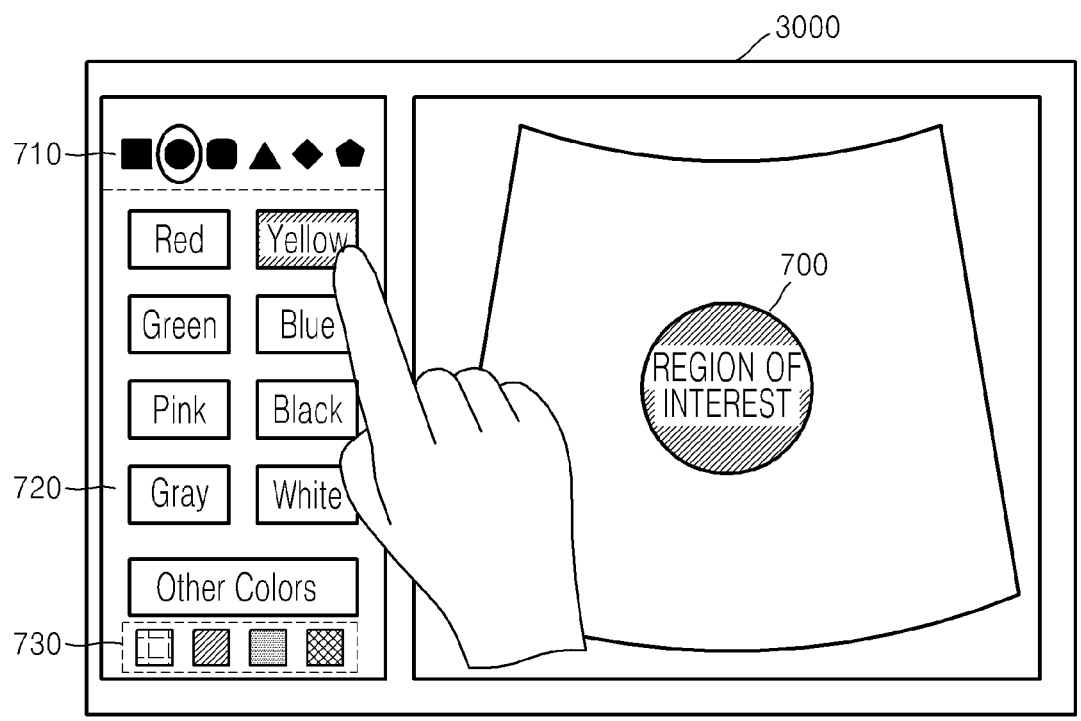
FIG. 7 is a diagram showing a GUI for marking a region of interest according to an exemplary embodiment.

FIG. 7 is a diagram showing a GUI for displaying an identification mark on a region of interest, according to an exemplary embodiment.

As shown in FIG. 7, the ultrasound apparatus 3000 of an exemplary embodiment may provide a template list 710 for selecting a region of interest 700. The template may be a figure that is set in advance and used to select the region of interest 700. The template list 710 according to an exemplary embodiment may include a circle, a square, a pentagon, etc.

For example, if the user selects a circle from the template list 710, the user may select the region of interest 700 by changing a location and a size of the circle on the ultrasound image.

According to another exemplary embodiment, the user may select the region of interest 700 by directly drawing a line on the ultrasound image by using a touch tool (for example, a finger, and an electronic pen), a mouse, or a trackball.

The ultrasound apparatus 3000 of an exemplary embodiment may provide a color list 720 for adding a color to the region of interest 700. The ultrasound apparatus 3000 according to another exemplary embodiment may provide a pattern list 730 so that the user may add a pattern to the region of interest 700. The user (for example, the technician) may add the color or the pattern to the region of interest 700 so as to help the patient's comprehension.

Figure 8:
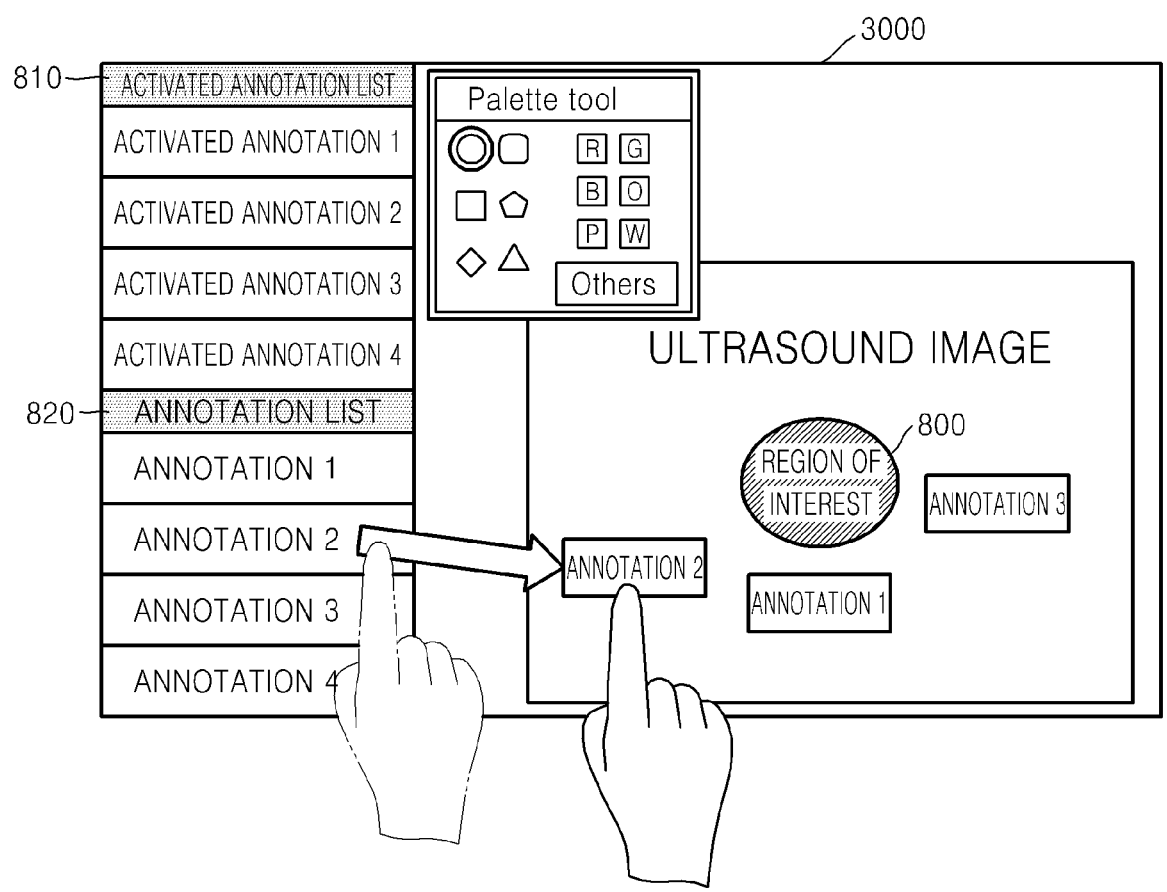
FIG. 8 is a diagram showing a GUI for adding an annotation and a color, according to an exemplary embodiment.

FIG. 8 is a diagram showing a GUI for adding an annotation and a color, according to an exemplary embodiment.

As shown in FIG. 8, the ultrasound apparatus 3000 may provide an activated annotation list 810, an annotation list 820, and a palette tool 830. The user (for example, the technician) may add an annotation for describing the ultrasound image. The user (for example, the technician) may select the region of interest 800 in the ultrasound image, and may indicate an identification mark on the region of interest 800 by using the palette tool 830.

The ultrasound apparatus 3000 of an exemplary embodiment may transmit first ultrasound information corresponding to the sharing level of the first device 1000 to the first device 1000. If the first device 1000 is the patient device, the sharing level information of the first device 1000 may be set in advance to share the annotation and the identification mark on the ultrasound image, as well as the ultrasound image, with the first device 1000. Therefore, the ultrasound apparatus 3000 of an exemplary embodiment may transmit the first ultrasound information including the annotation and the identification mark on the region of interest for helping the patient's comprehension of the ultrasound image to the first device 1000.

Figure 9:
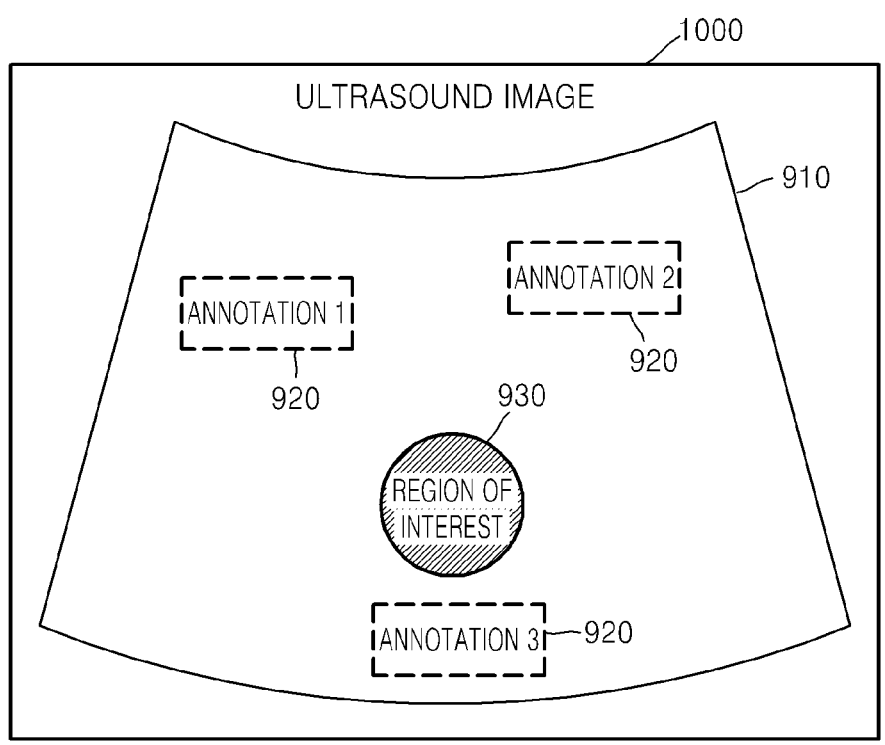
FIG. 9 is a diagram showing a screen of a device according to an exemplary embodiment.

FIG. 9 is a diagram showing a screen of the first device 1000, according to an exemplary embodiment.

As shown in FIG. 9, the first device 1000 of an exemplary embodiment may display the first ultrasound information transmitted from the ultrasound apparatus 3000 on the screen. The first ultrasound information displayed on the screen may include an ultrasound image 910, an annotation 920 for describing the ultrasound image 910, and a region of interest 930 indicated with an identification mark.

For example, if the ultrasound image 910 is an image of an embryo, the first device 1000 may display skin color on the image of the embryo so that the user may identify the embryo easily. The first device 1000 may display information about a head girth of the embryo, a location of the head, etc., as an annotation so that the patient may easily understand the image.

Therefore, the patient may understand the ultrasound image captured by the ultrasound apparatus 3000 through the first ultrasound information displayed on the first device 1000.

Hereinafter, processes of sharing the second ultrasound information between the ultrasound apparatus 3000 and the second device 2000 will be described with reference to FIGS. 10 through 13.

Figure 10:
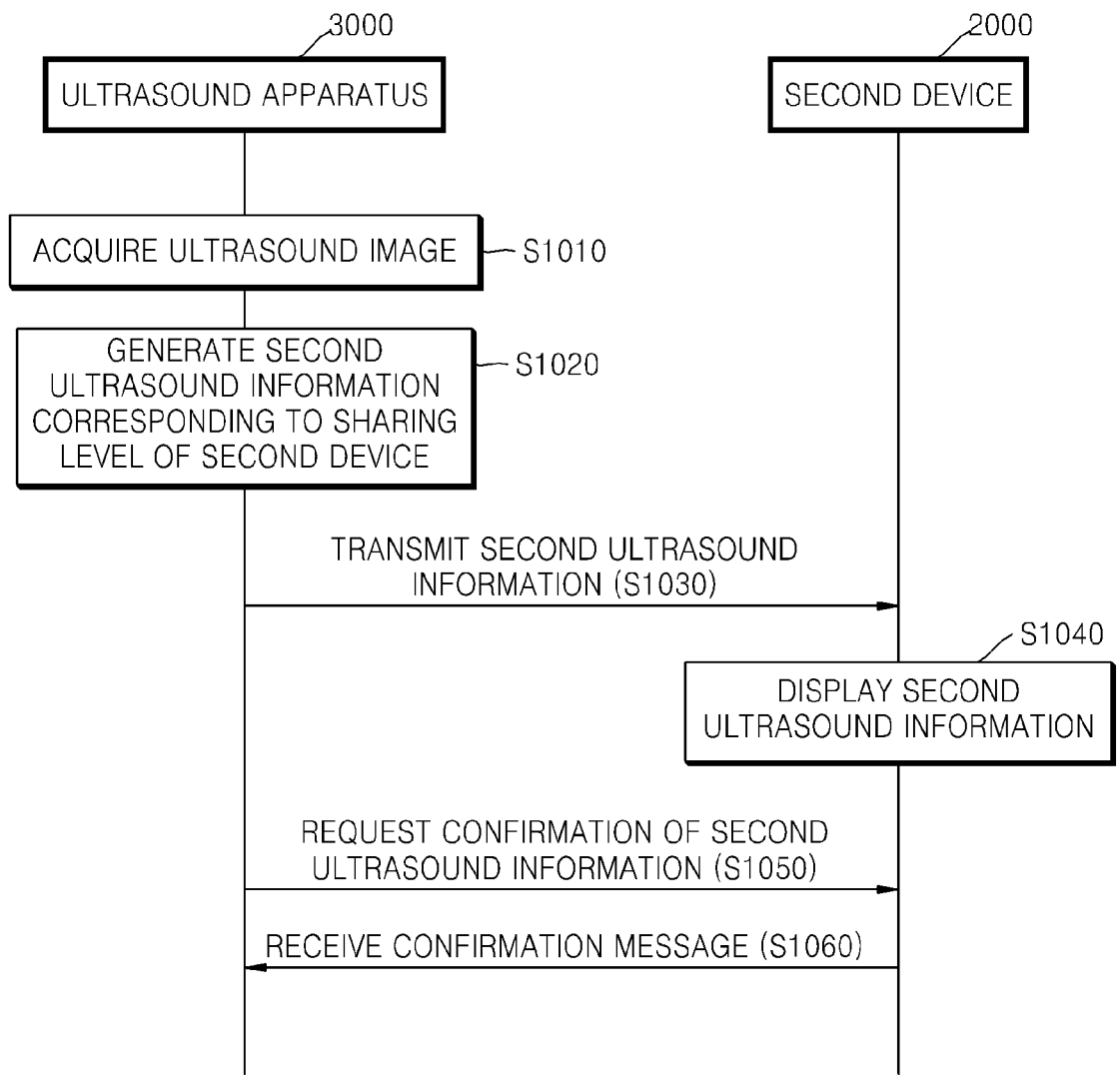
FIG. 10 is a flowchart illustrating a communication method according to the exemplary embodiment.

FIG. 10 is a flowchart illustrating a communication method between the ultrasound apparatus 3000 and the second device 1000, according to an exemplary embodiment.

In operation S1010, the ultrasound apparatus 3000 may acquire an ultrasound image about an object. Since operation S1010 corresponds to operation S310 shown in FIG. 3, detailed descriptions thereof will not be provided here.

In operation S1020, the ultrasound apparatus 3000 may generate second ultrasound information corresponding to the sharing level of the second device 2000. For example, if the second device 2000 is a medical expert device, the ultrasound apparatus 3000 may generate the second ultrasound information including an ultrasound image, measurement information of the ultrasound image, analysis information of the technician about the ultrasound image, and the patient information. Since operation S1020 corresponds to operation S470 of FIG. 4, detailed descriptions thereof will not be provided.

In operation S1030, the ultrasound apparatus 3000 may transmit the second ultrasound information to the second device 2000. According to an exemplary embodiment, the ultrasound apparatus 3000 may transmit the second ultrasound information to the second device 2000 via short distance communication. Examples of the short distance communication may include Wi-Fi, near field communication (NFC), Bluetooth, BLE, Zigbee, WFD, and UWB; however, the exemplary embodiments are not limited thereto.

In operation S1040, the second device 2000 receives the second ultrasound information transmitted from the ultrasound apparatus 3000, and may display the second ultrasound information on a screen. The medical expert (for example, a doctor) may identify the ultrasound image acquired by the ultrasound apparatus 3000 via the second device 2000 and may identify the analysis information of the technician, the measurement information of the ultrasound image, and the patient information included in the second ultrasound information to accurately diagnose a medical condition of the patient.

In operation S1050, the ultrasound apparatus 3000 may transmit a request for confirmation of the second ultrasound information to the second device 2000. For example, the ultrasound apparatus 3000 may request a confirmation of the medical expert for the ultrasound image or the analysis information of the technician included in the second ultrasound information.

In operation S1060, the second device 2000 may transmit a message for confirming the second ultrasound information to the ultrasound apparatus 3000 in response to the request for confirmation. For example, the second device 2000 may receive confirmation information of the ultrasound image from the medical expert, and may transmit the received confirmation information to the ultrasound apparatus 3000.

According to an exemplary embodiment, when receiving the confirmation message, the ultrasound apparatus 3000 may represent that the ultrasound image displayed on the screen is confirmed by the medical expert.

According to exemplary embodiments, an order of performing operations S1010 to S1060 may be changed, and some of the operations may be omitted.

Hereinafter, a method of confirming the second ultrasound information will be described in more detail with reference to FIGS. 11A and 11B.

Figure 11A:
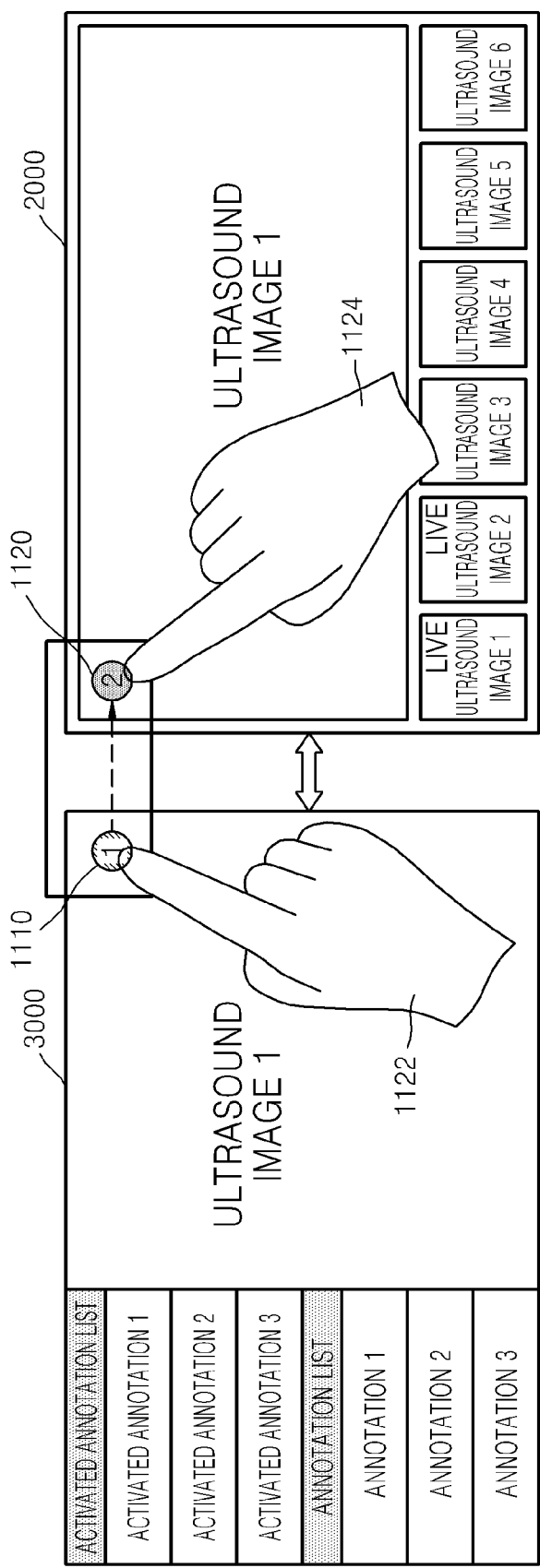
FIGS. 11A and 11B are diagrams showing a GUI for confirming an ultrasound image, according to an exemplary embodiment.
Figure 11B:
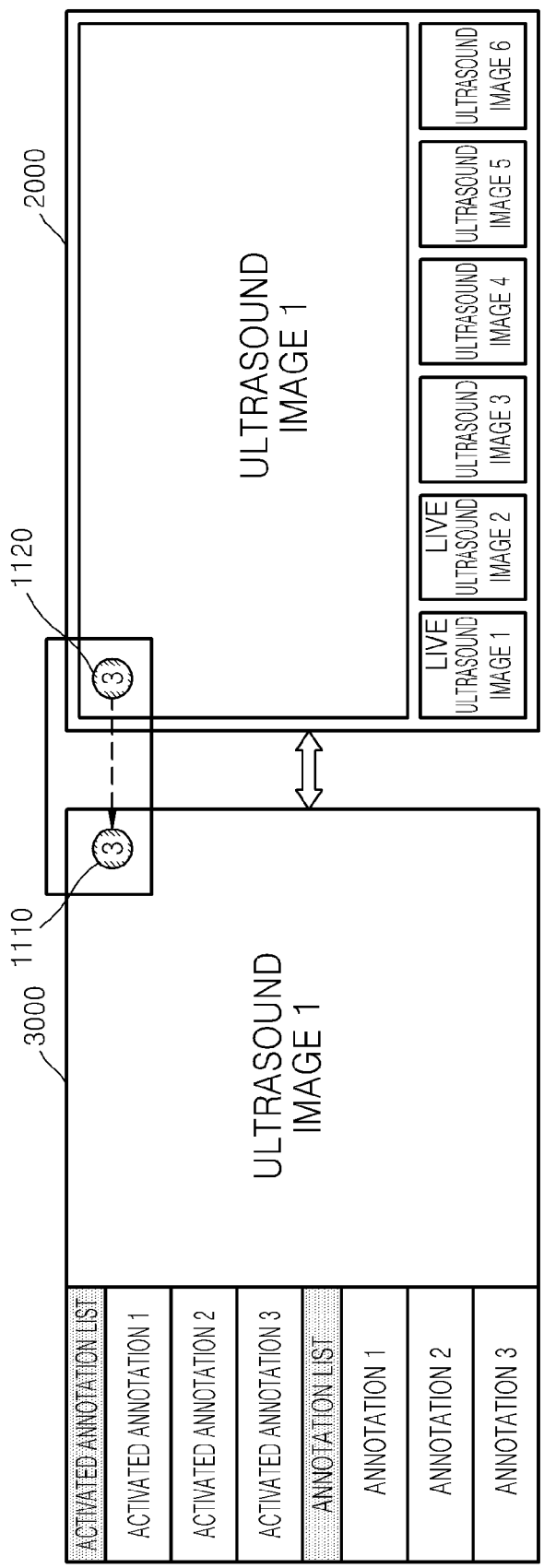

FIGS. 11A and 11B are diagrams showing a GUI for confirming the ultrasound image according to the exemplary embodiment. It is assumed that the second device 2000 is the medical expert device.

As shown in FIG. 11A, the ultrasound apparatus 3000 and the second device 2000 may respectively include confirmation buttons 1110 and 1120 for confirming the ultrasound image. The confirmation buttons 1110 and 1120 of an exemplary embodiment may be a GUI.

The confirmation buttons 1110 and 1120 of an exemplary embodiment may display the confirmation status processing by using a predetermined color, a predetermined number, and/or a predetermined pattern. For example, when the technician 1122 requests confirmation of an ultrasound image 1, the confirmation button 1110 may be displayed as a red ① button, on the ultrasound apparatus 3000. The confirmation button 1120 may be displayed as a blue ② button on the second device 2000. When the medical expert 1124 selects the blue confirmation button 1120 to confirm the ultrasound image 1, the confirmation button 1110 on the ultrasound apparatus 3000 and the confirmation button 1120 on the second device 2000 may be changed to be displayed as green ③ buttons, as shown in FIG. 11B.

According to another exemplary embodiment, the technician may additionally confirm the ultrasound image 1 after the medical expert confirms the ultrasound image 1. Here, after confirmations of both the medical expert and the technician in regard to the ultrasound image 1 are completed, the confirmation button 1110 on the ultrasound apparatus 3000 and the confirmation button 1120 on the second device 2000 may be changed to be displayed as the green ③ buttons.

According to an exemplary embodiment, since the ultrasound image used to diagnose the disease is confirmed only when both the technician and the medical expert confirm the ultrasound image, confirmation of a wrong ultrasound image due to a mistake of the technician or the medical expert may be prevented.

Figure 12:
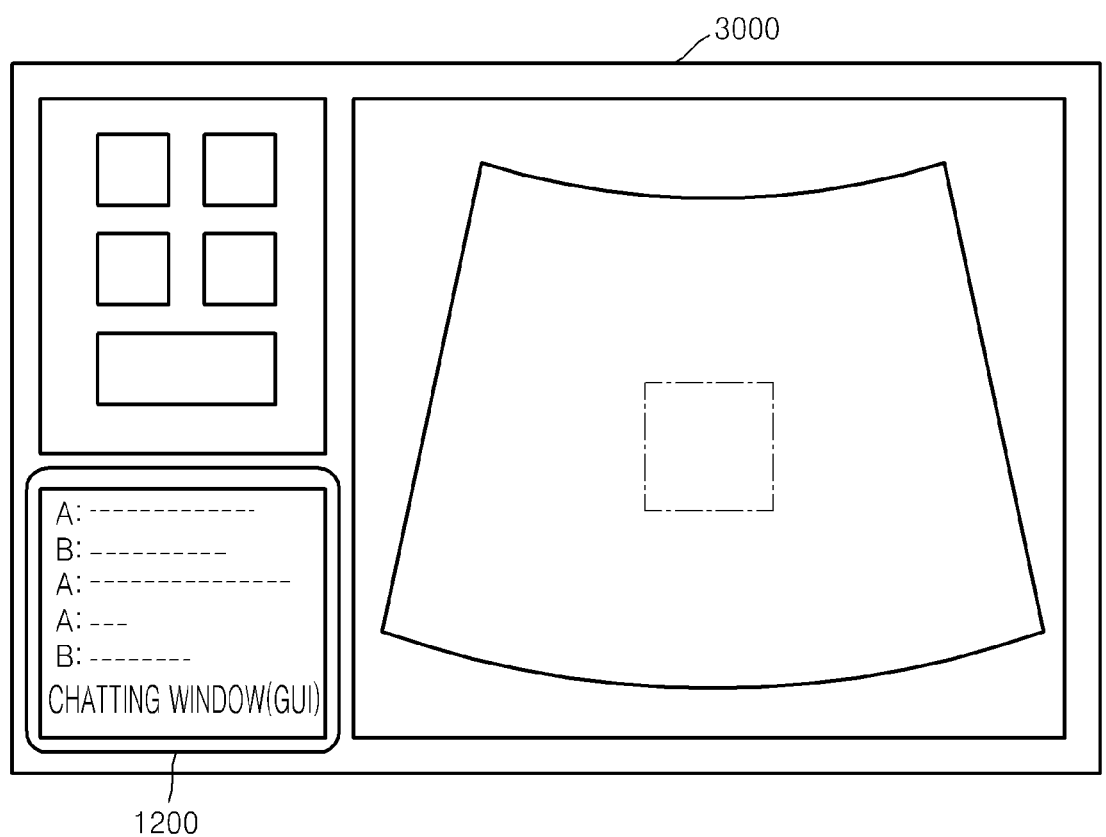
FIG. 12 is a diagram showing a screen providing a chatting window, according to an exemplary embodiment.

FIG. 12 is a diagram showing a screen on which a chatting window is provided by the ultrasound apparatus 3000, according to an exemplary embodiment.

As shown in FIG. 12, the ultrasound apparatus 3000 may provide a chatting window 1200 through which communication with the medical expert having the second device 2000 may be performed. The ultrasound apparatus 3000 of an exemplary embodiment may receive a user input about the ultrasound image (for example, a question of the technician) via the chatting window 1200. The ultrasound apparatus 3000 may transmit the user input (for example, the question of the technician) to the second device 2000, and may receive a response message with respect to the user input from the second device 2000.

For example, the ultrasound apparatus 3000 may receive inquiry information about a status of the patient (for example, arrhythmia, dyspnea, and posture of the patient) during the examination through the chatting window 1200 from the technician, and may transmit the inquiry information about the status of the patient to the second device 2000. The ultrasound apparatus 3000 receives an order of the medical expert about an action that has to be performed from the second device 2000 in consideration of the status of the patient, and may display the action ordered by the medical expert on the chatting window 1200.

Figure 13:
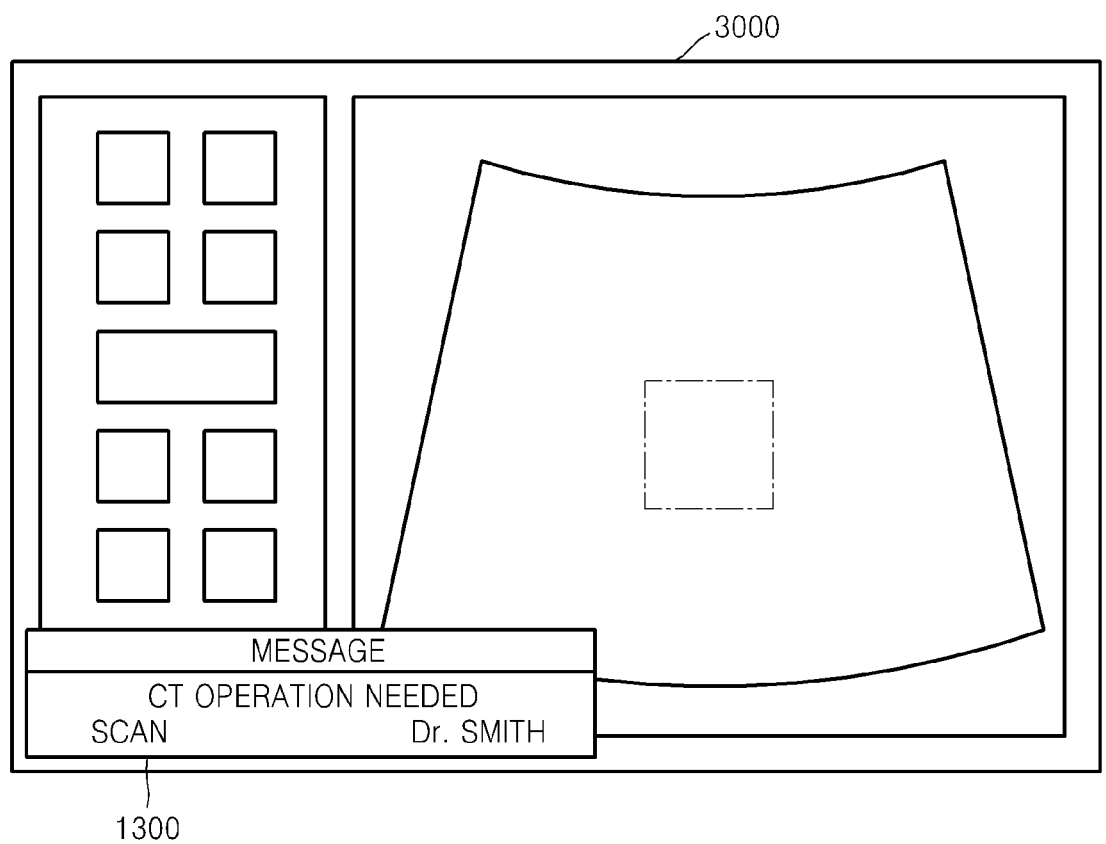
FIG. 13 is a diagram showing a screen displaying a message, according to an exemplary embodiment.

FIG. 13 is a diagram showing a screen displaying a message in the ultrasound apparatus 3000, according to an exemplary embodiment.

The ultrasound apparatus 3000 of an exemplary embodiment may receive a message about the ultrasound image from the second device 2000. The ultrasound apparatus 3000 may display the received image on the screen.

The ultrasound apparatus 3000 may display the message (for example, a message 'CT scan needed') transmitted from the second device 2000 as a pop-up window 1300.

According to an exemplary embodiment, the ultrasound apparatus 3000 may also receive a voice message and may output the voice message through a speaker.

Figure 14:
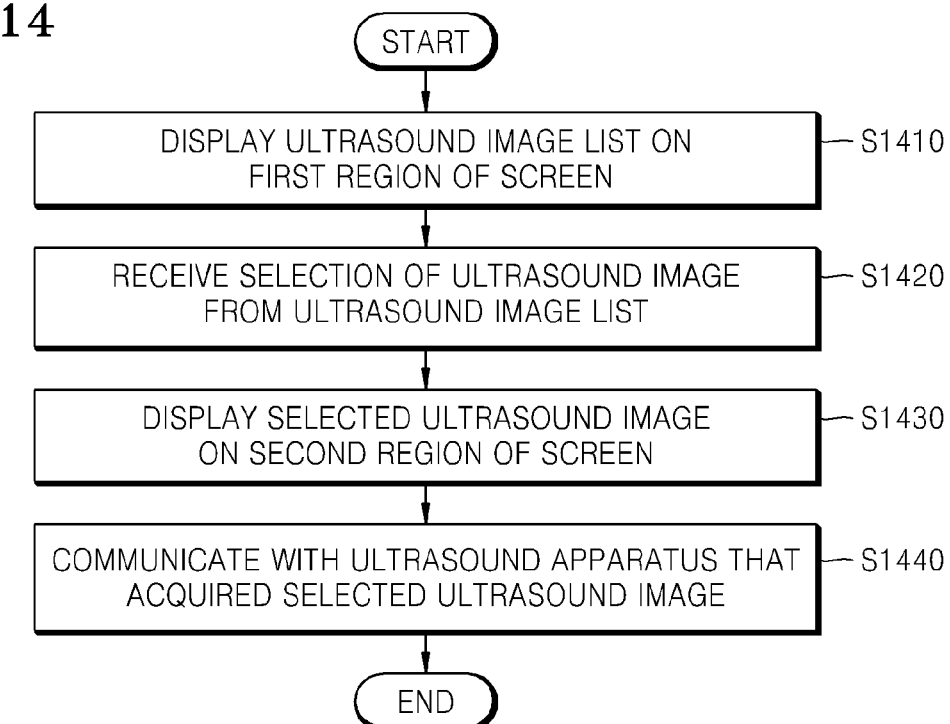
FIG. 14 is a flowchart illustrating a communication method, according to an exemplary embodiment.

FIG. 14 is a flowchart illustrating a communication method of the second device 2000, according to an exemplary embodiment.

In operation S1410, the second device 2000 may display an ultrasound image list on a first region of the screen. For example, the second device 2000 may display an ultrasound image list including at least one ultrasound image acquired by at least one ultrasound apparatus on the first region of the screen. The ultrasound image list according to an exemplary embodiment may include thumbnail images of the ultrasound images.

The ultrasound image list of an exemplary embodiment may include real-time ultrasound images transmitted from at least one ultrasound apparatus, and ultrasound images that are stored in advance. The real-time ultrasound image may denote an ultrasound image acquired by the ultrasound apparatus 3000 within a predetermined time period prior to the current time or the time point when the ultrasound image is received by the second device 2000. For example, the real-time ultrasound image may be an image acquired by the ultrasound apparatus 3000 within 10 minutes from the time point when the ultrasound image is received by the second device 2000. That is, when the predetermined time is 10 minutes, the ultrasound image acquired 3 minutes earlier is a real-time image, whereas the ultrasound image acquired 15 minutes earlier may not be a real-time image.

The ultrasound image stored in advance may be an image acquired by the ultrasound apparatus 3000 prior to the predetermined time period and stored. According to an exemplary embodiment, the ultrasound image may be stored in the ultrasound apparatus 3000, the server 4000, and/or the second device 2000. Therefore, the second device 2000 may read the ultrasound images stored in advance from a memory of the ultrasound apparatus 3000, the server 4000, or the second device 2000.

According to an exemplary embodiment, the second device 2000 may indicate an identification mark on the real-time ultrasound image in order to distinguish the real-time ultrasound image and the ultrasound image stored in advance from each other. For example, the second device 2000 may add an indicator such as 'LIVE' or an exclamation mark (!) to the real-time ultrasound image in the ultrasound image list, make a boundary of the real-time ultrasound image bold, or display the boundary of the real-time ultrasound image in a predetermined color. The second device 2000 may display the real-time ultrasound image to be larger than the ultrasound image stored in advance or may locate the real-time ultrasound image at a center portion in the ultrasound image list.

In operation S1430, the second device 2000 may receive a selection of an ultrasound image from the ultrasound image list. For example, when the second device 2000 includes a touch screen, the second device 2000 senses a medical expert gesture such as a tap, a double-tap, a flicking, or a dragging operation of the ultrasound image included in the ultrasound image list to receive a selection of the medical expert on one ultrasound image from the ultrasound image list.

Otherwise, if the screen on which the ultrasound image list is displayed is not a touch screen, the medical expert may select one ultrasound image from the ultrasound image list by using a mouse or a trackball, or by a voice input.

In operation S1440, the second device 2000 may display the selected ultrasound image on a second region of the screen. The second device 2000 of an exemplary embodiment may display the selected ultrasound image on the second region in a predetermined size. That is, the second device 2000 may display the ultrasound image to be greater than the thumbnail image included in the ultrasound image list on the second region.

The second device 2000 according to an exemplary embodiment may further display at least one of the analysis information of the technician about the ultrasound image displayed on the second region, measurement information of the ultrasound image displayed on the second region, and the patient information according to the sharing level.

In operation S1440, the second device 2000 may communicate with the ultrasound apparatus 3000 that acquired the selected ultrasound image.

For example, the second device 2000 according to an exemplary embodiment may provide a chatting window for communicating with the ultrasound apparatus 3000 on a third region of the screen. The second device 2000 may receive an input of the medical expert about the ultrasound image displayed on the second region, through the chatting window. The second device 2000 may transmit the input of the medical expert received through the chatting window to the ultrasound apparatus 3000 in a chatting session.

The second device 2000 according to an exemplary embodiment may receive a request for confirming the selected ultrasound image from the ultrasound apparatus 3000 second device 2000 and may transmit the confirmation information to the ultrasound apparatus 3000 when the confirmation information about the selected ultrasound image is input.

The second device 2000 of an exemplary embodiment may transmit control information for controlling the ultrasound apparatus 3000 to the ultrasound apparatus 3000. The control information of an exemplary embodiment may include at least one of a control command for selecting and displaying another ultrasound image that is different from the ultrasound image displayed on the second region, a control command for expanding or reducing the ultrasound image displayed on the second region, a control command for storing the ultrasound image displayed on the second region, a control command for 3D rendering the ultrasound image displayed on the second region, a control command for adding an annotation or a body marker to the ultrasound image displayed on the second region, a control command for measuring a region of interest, and a control command for correcting analysis information of the ultrasound image displayed on the second region.

Hereinafter, a screen for displaying a plurality of ultrasound images acquired by a plurality of ultrasound apparatuses in the second device 2000 will be described with reference to FIGS. 15 through 18.

Figure 15:
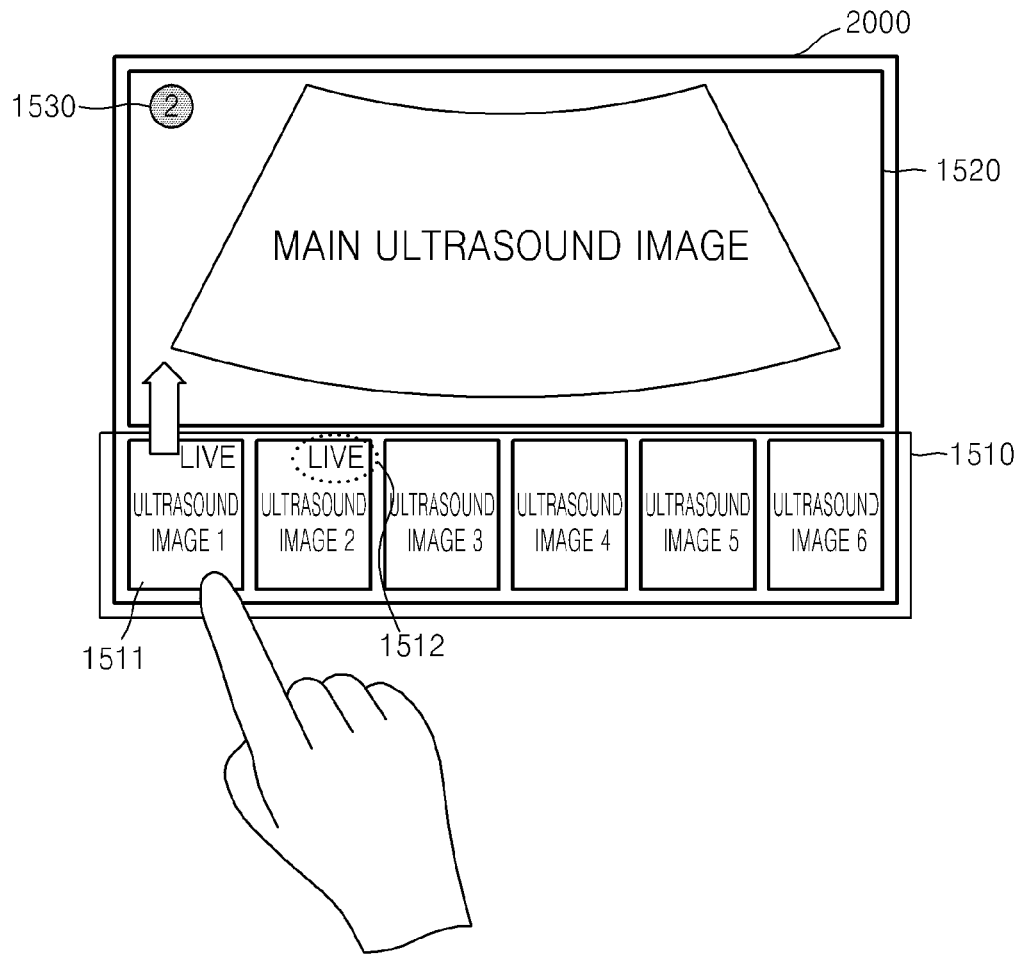
FIG. 15 is a diagram showing a screen providing a list of ultrasound images, according to an exemplary embodiment.

FIG. 15 is a diagram showing a screen providing an ultrasound image list by the second device 2000, according to an exemplary embodiment.

As shown in FIG. 15, the screen of the second device 2000 according to an exemplary embodiment may be divided into a first region 1510 for displaying an ultrasound image list and a second region 1520 displaying a main ultrasound image.

The ultrasound image list may include the real-time ultrasound images acquired by the ultrasound apparatus 3000 and/or the ultrasound images stored in advance. The second device 2000 of an exemplary embodiment may distinguish the ultrasound images stored in advance and the real-time ultrasound images from each other by a mark 'LIVE' 1512 added to the real-time ultrasound images. For example, an ultrasound image 1511 and an ultrasound image 1512 are the real-time ultrasound images. An ultrasound image 3, an ultrasound image 4, an ultrasound image 5, and an ultrasound image 6 may be the ultrasound images that are stored in advance and/or the ultrasound images that are not real-time.

According to an exemplary embodiment, when a touch-and-drag input, in which the medical expert drags the ultrasound image 1511 to the second region 1520 while touching the ultrasound image 1511, is sensed, the second device 2000 may display the ultrasound image 1511 on the second region 1520 as a main ultrasound image. FIG. 15 shows the touch-and-drag gesture as an example of selecting the ultrasound image; however, the exemplary embodiments are not limited thereto. For example, the doctor may select the ultrasound image by using a tap gesture, a double tap gesture, a voice input, or a physical selection button.

The second device 2000 of an exemplary embodiment communicates with the ultrasound apparatus 3000 that acquires the ultrasound image 1511 bi-directionally. This will be described below with reference to FIG. 16.

The second device 2000 may display a GUI for receiving a confirmation input of the ultrasound image 1511, that is, a confirmation button 1530, on the screen. The second device 2000 may receive a confirmation input of the medical expert about the ultrasound image 1511 via the confirmation button 1530. When the medical expert selects the confirmation button 1530 to confirm the ultrasound image 1511, a color and/or a pattern of the confirmation button 1530 may be changed. The second device 2000 may transmit a confirmation message of the ultrasound image 1511 to the ultrasound apparatus 3000 that acquired the ultrasound image 1511.

Figure 16:
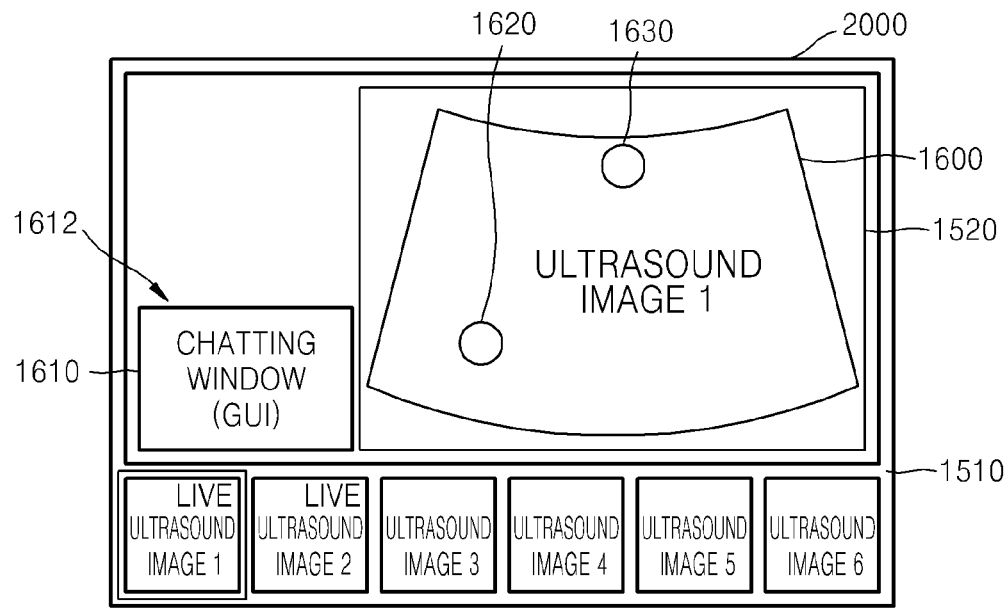
FIG. 16 is a diagram showing a screen displaying a chatting window and a pointer, according to an exemplary embodiment.

FIG. 16 is a diagram showing a screen for displaying a chatting window and a pointer in the second device 2000, according to an exemplary embodiment. In FIG. 16, it is assumed that the medical expert is a doctor.

As shown in FIG. 16, the second device 2000 of an exemplary embodiment may provide a chatting window 1610 for communicating with the ultrasound apparatus 3000 on a third region 1612 of the screen. The second device 2000 may receive an input of the doctor about an ultrasound image 1600 via the chatting window 1610, and may transmit the received input to the ultrasound apparatus 3000.

The second device 2000 of an exemplary embodiment may receive an image message, a voice message, and a text message of the technician from the ultrasound apparatus 3000, and may transmit an image message, a voice message, and a text message of the medical expert to the ultrasound apparatus 3000 via the chatting window 1610.

For example, the doctor may identify a result report generated by the technician after performing the ultrasound examination and may confirm that the report may be finished in the current status, or may input a message requesting correction of a result value of the report in the chatting window 1610.

Also, if the ultrasound image is not exact and measurement information with respect to the ultrasound image is insufficient, a message requesting a re-examination may be input to the chatting window 1610. The doctor may request the technician to perform an examination such as CT or MRI.

In addition, since the measured values may vary depending on the status of the patient, the doctor may inquire about the technician's opinion regarding the measurement values or may ask the technician about an operation status of the patient via the chatting window 1610.

According to an exemplary embodiment, the second device 2000 may display a first pointer 1630 of the ultrasound apparatus 3000 and a second pointer 1620 of the second device 2000 on the ultrasound image 1600 displayed on the second device 2000. The second device 2000 may receive information about a location of the first pointer 1630 of the ultrasound apparatus 3000 from the ultrasound apparatus 3000.

Also, the ultrasound apparatus 3000 may display the first pointer 1630 of the ultrasound apparatus 3000 and the second pointer 1620 of the second device 2000 on the ultrasound image 1600 displayed on the ultrasound apparatus 3000. Therefore, the technician and the doctor may identify areas of interest of each other by locating the pointer on a point of interest via the bi-directional chatting, in real time.

Figure 17:
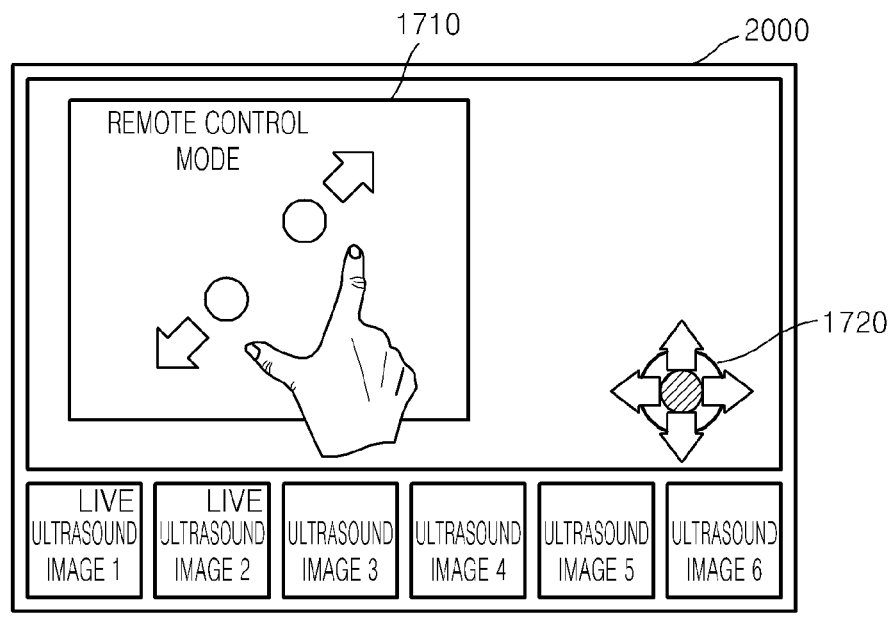
FIG. 17 is a diagram showing an example of a GUI for remotely controlling the ultrasound apparatus, according to the exemplary embodiment.

FIG. 17 is a diagram showing an example of a GUI for remotely controlling the ultrasound apparatus 3000 by the second device 2000, according to an exemplary embodiment.

The second device 2000 of an exemplary embodiment may sense a pinch input on a main ultrasound image 1710. The second device 2000 may transmit a control command for expanding or reducing the main ultrasound image 1710 to the ultrasound apparatus 3000 based on the pinch input.

For example, when the user touches the screen with two fingers and increases a distance between the fingers, a control command for expanding the main ultrasound image 1710 according to the distance between the fingers is transmitted to the ultrasound apparatus 3000. Otherwise, when the user touches the screen with two fingers and reduces the distance between the fingers, a control command for reducing the main ultrasound image 1710 may be transmitted to the ultrasound apparatus 3000.

When the main ultrasound image 1710, which is displayed on the second device 2000, is expanded or reduced on the second device 2000, a resolution of the displayed ultrasound image may be lowered. Thus, the second device 2000 remotely controls the ultrasound apparatus 3000 to expand or reduce the main ultrasound image 1710 and to transmit the expanded or reduced ultrasound image to the second device 2000 in real-time, while maintaining the resolution.

According to an exemplary embodiment, the second device 2000 may transmit a control command for adjusting a direction of a probe to the ultrasound apparatus 3000 based on the medical expert's input. For example, the second device 2000 may include a remote controller and may remotely control the probe direction of the ultrasound apparatus 3000 according to the medical expert's input, by manipulating a remote control button 1720 displayed on the screen to an upper/lower/left/right position, or another position therebetween.

Figure 18A:
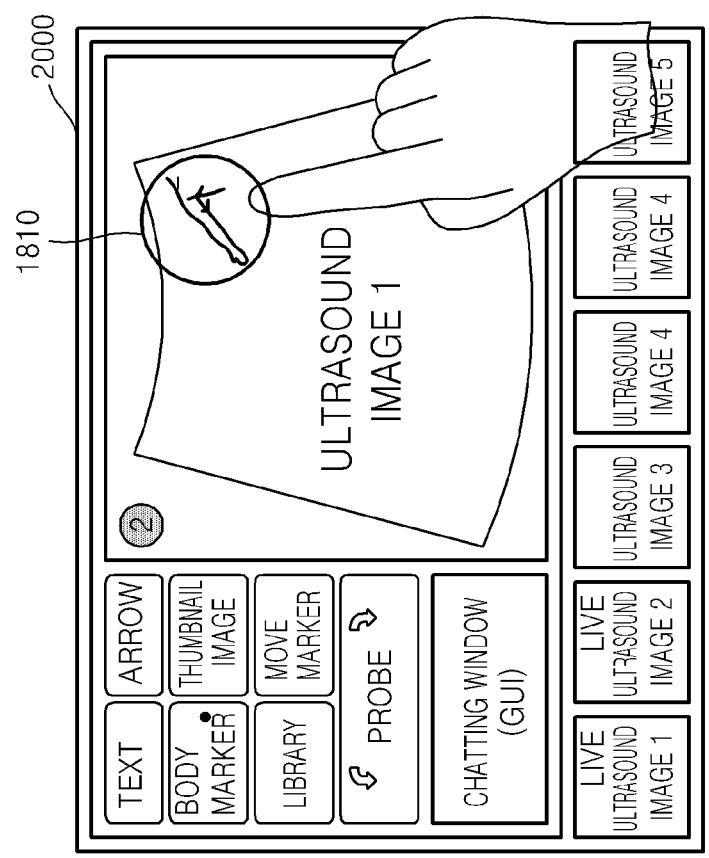
FIGS. 18A and 18B are diagrams showing an example of a GUI for adding a body marker to the ultrasound image remotely, according to the exemplary embodiment.
Figure 18B:
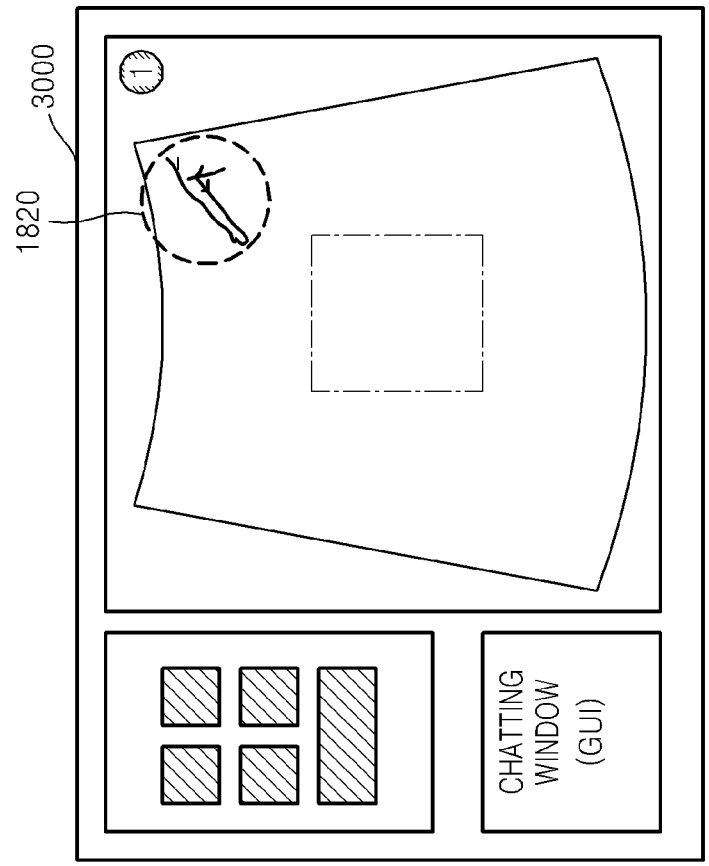

FIGS. 18A and 18B are diagrams showing an example of a GUI for adding a body marker to the ultrasound image remotely by the second device 2000, according to an exemplary embodiment.

The body marker according to an exemplary embodiment may be a figure for identifying a location to which an ultrasound wave is scanned or an object. The body marker of an exemplary embodiment may include a figure representing an object to which the ultrasound wave is scanned and a figure representing a location of the probe contacting the object. An example of the body marker may be an arm shape, a liver shape, or a uterus shape.

As shown in FIG. 18A, the second device 2000 may receive an input of the medical expert for adding a body marker 1810 to the ultrasound image. In this case, the second device 2000 may transmit to the ultrasound apparatus 3000 a control command for adding the body marker 1810 selected by the medical expert to the ultrasound image displayed on the ultrasound apparatus 3000.

As shown in FIG. 18B, the ultrasound apparatus 3000 receives the control command for adding the body marker from the second device 2000, and may add a body marker 1820 to the ultrasound image displayed on the screen.

According to an exemplary embodiment, the medical expert may control the ultrasound apparatus 3000 via the second device 2000 from a remote distance.

FIGS. 18A and 18B show an example of a GUI for adding the body marker; however, the exemplary embodiments are not limited thereto. For example, the second device 2000 may remotely control the ultrasound apparatus 3000 to add an annotation, to re-measure the region of interest, or to perform 3D image rendering.

The second device 2000 may control the ultrasound apparatus 3000 to display a certain ultrasound image, and thus, the medical expert may select and display a desired ultrasound image from the thumbnail images or review window displayed on the ultrasound apparatus 3000, and then, check the selected ultrasound image. The medical expert may expand another ultrasound image while reviewing the selected ultrasound image.

The medical expert may control the ultrasound apparatus 3000 remotely to store the ultrasound image again, or may directly correct the report generated by the technician.

Figure 19:
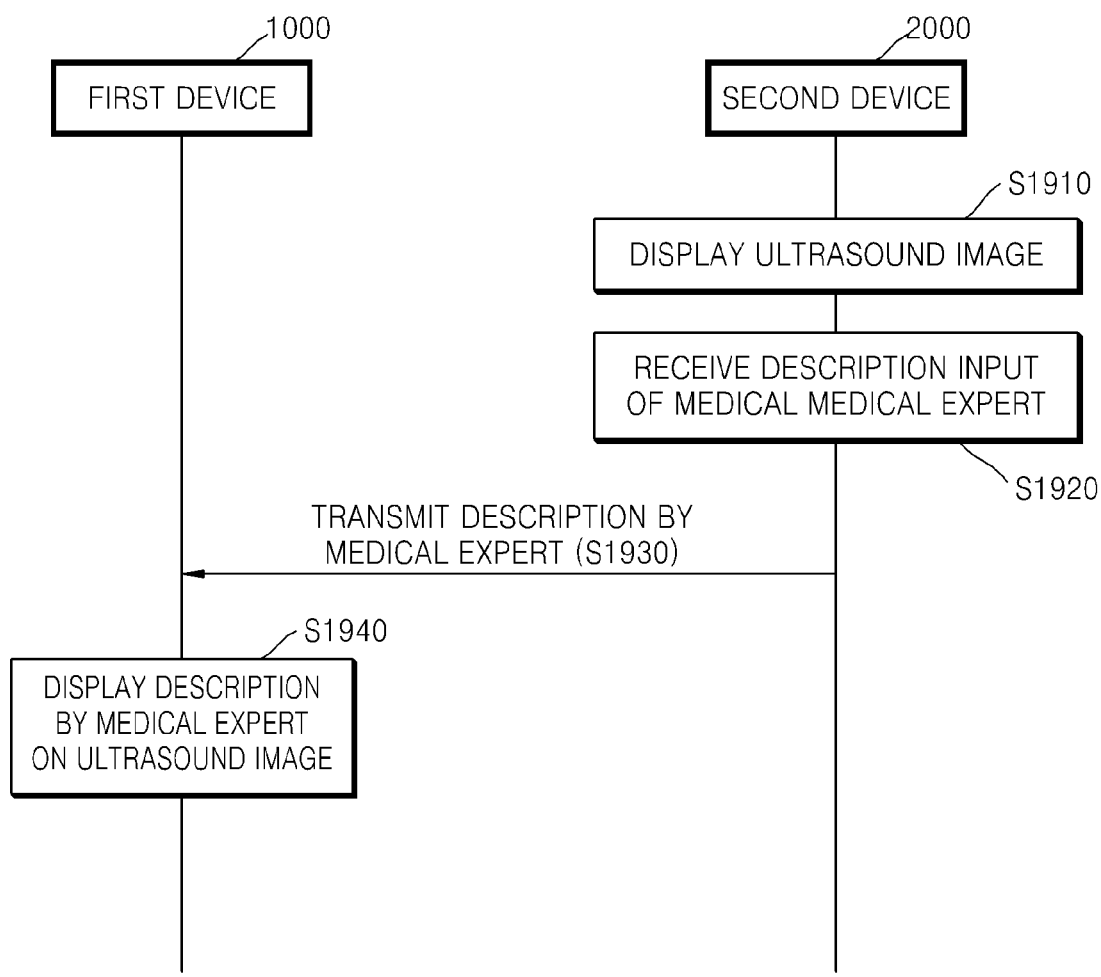
FIG. 19 is a flowchart illustrating a communication method, according to the exemplary embodiment.

FIG. 19 is a flowchart illustrating a communication method between the second device 2000 and the patient device, according to an exemplary embodiment. In FIG. 19, it is assumed that the second device 2000 is the medical expert device, and the first device 1000 is the patient device.

In operation S1910, the second device 2000 may display an ultrasound image on the screen. According to an exemplary embodiment, the ultrasound image displayed on the second device 2000 may be an ultrasound image acquired by the ultrasound apparatus 3000 in real-time, or an ultrasound image stored in a memory in advance.

In operation S1920, the second device 2000 may receive a description, from the medical expert, about the ultrasound image displayed on the screen. For example, the description by the medical expert may include representing a region of interest (for example, a tumor, an embryo, a head of the embryo, a hand of the embryo, etc.), a description about the region of interest, an analysis result of the measurement value (for example, head girth, the number of fingers of an embryo, etc.), or existence of lesions; however, the exemplary embodiments are not limited thereto.

In operation S1930, the second device 2000 may transmit the description of the medical expert to the first device 1000.

The first device 1000 may be a patient device displaying the ultrasound image that is the same as that displayed on the second device 2000.

According to an exemplary embodiment, the second device 2000 may transmit the description by the medical expert to the first device 1000 through wired or wireless communication. Otherwise, the second device 2000 may transmit the description by the medical expert to the first device 1000 via the server 4000.

According to an exemplary embodiment, the second device 2000 may transmit the description by the medical expert about the ultrasound image input from the medical expert to the ultrasound apparatus 3000. The second device 2000 may transmit the description by the medical expert simultaneously to both the first device 1000 and the ultrasound apparatus 3000, or may transmit them sequentially.

In operation S1940, the first device 1000 may display the received description by the medical expert on the ultrasound image which is displayed on the screen of the first device 1000.

According to an exemplary embodiment, the description by the medical expert may be displayed on the first device 1000 in real-time or may be stored in the first device 1000. Here, displaying of the description by the medical expert on the first device 1000 in real-time denotes that the description by the medical expert is displayed on the first device 1000 within a predetermined time period after the input of the description to the second device 2000.

Figure 20:
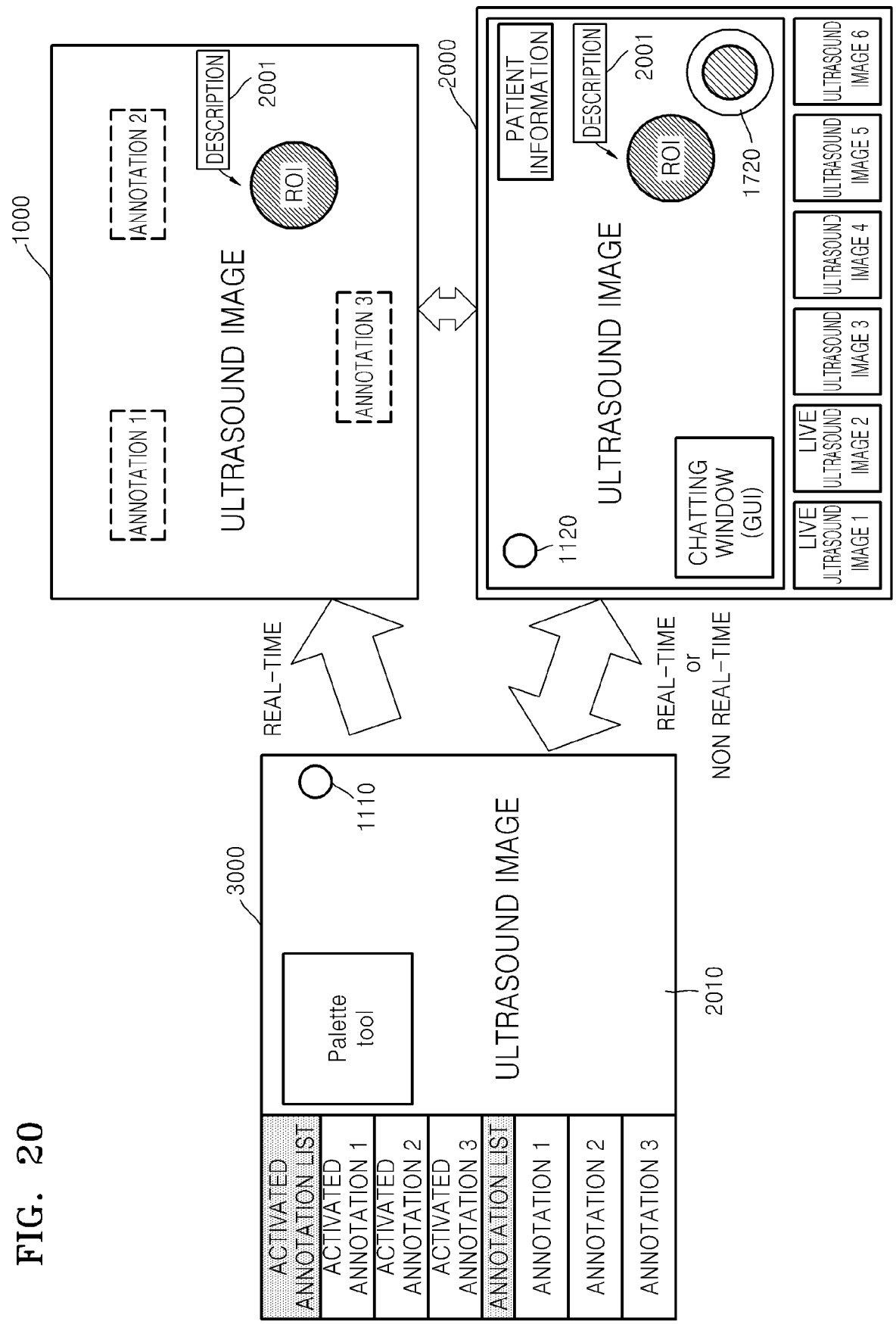
FIG. 20 shows screens of the ultrasound apparatus, the first device, and the second device according to the exemplary embodiment.

FIG. 20 shows screens of the ultrasound apparatus 3000, the first device 1000, and the second device 2000, according to an exemplary embodiment.

The ultrasound apparatus 3000 may transmit the ultrasound image displayed on the screen 2010 to the first device 1000 and the second device 2000 in real-time. The ultrasound apparatus 3000 may display a GUI for adding an annotation or color to the ultrasound image for the user of the first device 1000, and a confirmation button to request the confirmation of the ultrasound image from the second device 2000.

The ultrasound image displayed on the screen that the user (for example, the technician) of the ultrasound apparatus 3000 watches may be displayed on the first device 1000 and the second device 2000 in real-time. The information about the ultrasound image displayed on the first device 1000 and the second device 2000 may vary depending on the sharing levels of the first device 1000 and the second device 2000.

For example, the ultrasound image, the annotation for describing the ultrasound image, and the identification mark of the region of interest included in the ultrasound image may be displayed on the screen of the first device 1000 according to the sharing level of the first device 1000.

The ultrasound image, the information about the patient, the measurement information with respect to the ultrasound image, the chatting window for communicating with the user of the ultrasound apparatus 3000, the confirmation button for confirming the ultrasound image, and the GUI for remotely controlling the ultrasound apparatus 3000 may be displayed on the screen of the second device 2000 according to the sharing level of the second device 2000.

The second device 2000 may display information about a non-real time ultrasound image, as well as the real-time ultrasound image, on the screen thereof. For example, the second device 2000 displays the ultrasound image list including the real-time ultrasound image and the ultrasound image that is stored in advance on the first region of the screen, and may display one ultrasound image selected from the ultrasound image list on the second region of the screen.

According to an exemplary embodiment, when the user (for example, the medical expert) of the second device 2000 inputs a description 2001 about the ultrasound image, the second device 2000 may transmit the input description 2001 to the first device 1000. The first device 1000 may display the description 2001 transmitted from the second device 2000 on the ultrasound image.

Figure 21:
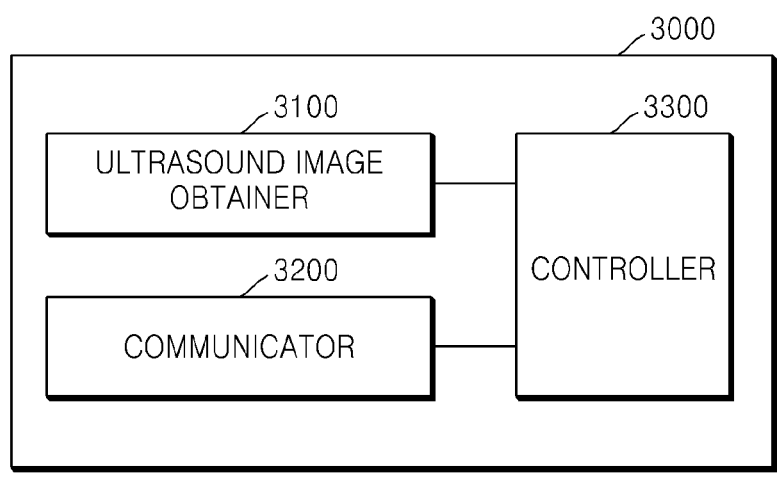
FIG. 21 is a block diagram showing an ultrasound apparatus according to an exemplary embodiment.
Figure 22:
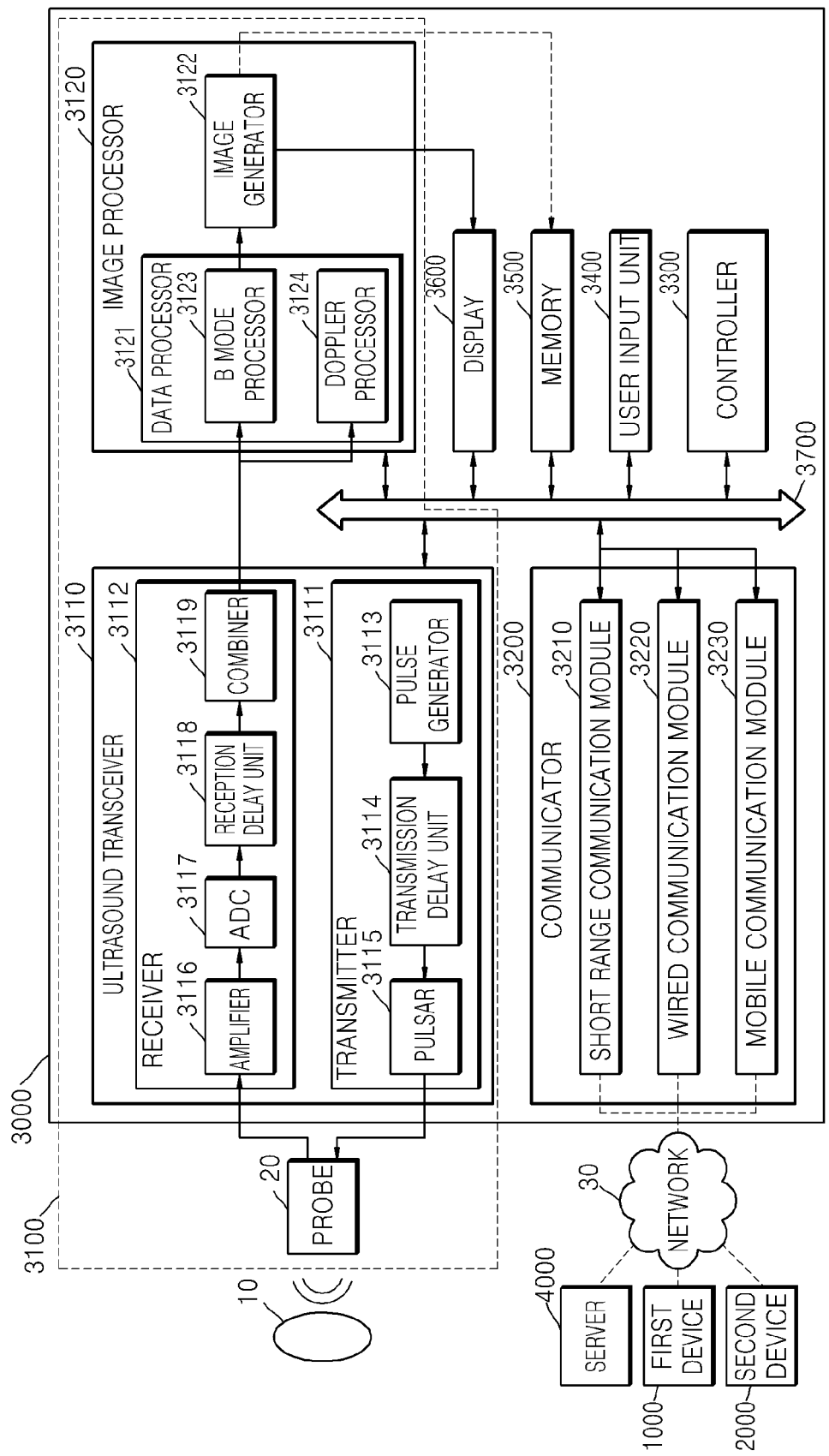
FIG. 22 is a block diagram showing an ultrasound apparatus according to another exemplary embodiment.

FIGS. 21 and 22 are block diagrams showing an ultrasound apparatus 3000, according to an exemplary embodiment.

As shown in FIG. 21, the ultrasound apparatus 3000 of an exemplary embodiment may include an ultrasound image obtainer 3100, a communicator 3200, and a controller 3300. However, not all the components shown in FIG. 21 may be essential elements. The ultrasound apparatus 3000 may include the illustrated elements and other elements, or may include only some of the illustrated elements.

As shown in FIG. 22, the ultrasound apparatus 3000 according to another exemplary embodiment may further include a user input unit 3400, a memory 3500, and a display 3600. The above components may be connected to each other via a bus 3700.

Hereinafter, the above components will be described.

The ultrasound image obtainer 3100 of an exemplary embodiment may acquire ultrasound image data about an object. The ultrasound image data may be 2D ultrasound image data or 3D ultrasound image data about the object.

According to an exemplary embodiment, the ultrasound image obtainer 3100 may include a probe 20, an ultrasound transceiver 3110, and an image processor 3120.

The probe 20 sends an ultrasound signal to an object 10 according to a driving signal applied from the ultrasound transceiver 3110, and receives an echo signal reflected by the object 10. The probe 20 may include a plurality of transducers that vibrate according to an electric signal to generate the ultrasound that is acoustic energy. The probe 20 may be connected to a main body of the ultrasound apparatus 3000 via a wire or wirelessly, and the ultrasound apparatus 3000 may include a plurality of probes 20 according to an exemplary embodiment. The probe 20 may include at least one of a one-dimensional (1D) probe, a 1.5-dimensional (1.5D) probe, a 2D (matrix) probe, and a 3D probe.

A transmitter 3111 applies a driving signal to the probe 20, and may include a pulse generator 3113, a transmission delay unit 3114, and a pulsar 3115. The pulse generator 3113 generates pulses for forming a transmission ultrasound according to a predetermined pulse repetition frequency (PRF), and the transmission delay unit 3114 applies a delay time for determining transmission directionality to the pulses. Each of the pulses to which the delay time is applied corresponds to each of a plurality of piezoelectric vibrators included in the probe 20. The pulsar 3115 applies the driving signal (or the driving pulse) to the probe 20 at timings corresponding to the pulses to which the delay time is applied.

A receiver 3112 processes an echo signal transmitted from the probe 20 to generate ultrasound data, and may include an amplifier 3116, an analog-to-digital converter (ADC) 3117, a reception delay unit 3118, and a combiner 3119. The amplifier 3116 amplifies the echo signal for each of channels, and the ADC 3117 converts the amplified echo signal. The reception delay unit 3118 applies a delay time for determining a reception directionality to the echo signal that is converted to a digital signal, and the combiner 3119 combines echo signals processed by the reception delay unit 3118 to output the ultrasound data to a data processor 3121.

The image processor 3120 generates ultrasound images by performing a scan conversion of the ultrasound data generated by the ultrasound transceiver 3110. The ultrasound image may include a gray scale image obtained by scanning the object in an amplitude (A) mode, a brightness (B) mode, and a motion (M) mode, and a Doppler image representing a moving object by using the Doppler effect. The Doppler image may include a bloodstream Doppler image (or color Doppler image) representing flow of blood, a tissue Doppler image representing movement of tissues, and a spectral Doppler image representing velocity of the object as a waveform.

A B mode processor 3123 extracts B mode components from the ultrasound data, and processes the B mode components. An image generator 3122 may generate an ultrasound image in which an intensity of a signal is represented by brightness based on the B mode components extracted by the B mode processor 3123.

Likewise, a Doppler processor 3124 extracts Doppler components from the ultrasound data, and the image generator 3122 may generate a Doppler image in which movement of the object is represented by a color or a waveform based on the extracted Doppler components.

The image generator 3122 according to an exemplary embodiment may generate a 3D ultrasound image by performing a volume rendering process of volume data, and may generate an elastic mode image in which a transformation degree of the object 10 according to a pressure is imaged.

The image generator 3122 may represent various pieces of additional information as a text or a graphic on the ultrasound image. For example, the image generator 3122 may add at least one annotation relating to all or some of the ultrasound image to the ultrasound image. That is, the image generator 3122 may analyze the ultrasound image, and may recommend at least one annotation relating to all or some of the ultrasound image based on a result of the analysis. The image generator 3122 may add at least one annotation selected by the user to the ultrasound image.

The image processor 3120 may extract a region of interest from the ultrasound image by using an image processing algorithm. The image processor 3120 may add a color, a pattern, or a boundary to the region of interest.

The communicator 3200 may include one or more components enabling communications between the ultrasound apparatus 3000 and the first device 1000, the ultrasound apparatus 3000 and the second device 2000, and the ultrasound apparatus 3000 and the server 4000. For example, the communicator 3200 may include a short range communication module 3210, a wired communication module 3220, a mobile communication module 3230, etc.

The short distance communication module 3210 refers to a module for short distance communication. As a short distance communication technology, WLAN (e.g., Wi-Fi), Bluetooth, BLE, UWB, ZigBee, NFC, WFD, Infrared Data Association (IrDA), etc. may be used.

The wired communication module 3220 is a communication module using an electric signal or an optical signal. As a wired communication technology of an exemplary embodiment, a pair cable, a coaxial cable, an optical fiber cable, an Ethernet cable, etc. may be used.

The mobile communication module 3230 transmits and receives wireless signals to and from at least one of a base station, an external device, and a server on a mobile communication network. The wireless signal may include various types of data according to a voice call signal, a video call signal, or text/multimedia message transmission.

The communicator 3200 is connected to a network 30 by using a wire or wirelessly to communicate with an external device (for example, the first device 1000 or the second device 2000) or the server 4000. The communicator 3200 may transmit and receive data to and from a hospital server or other medical equipment in the hospital, which are connected to the communicator 3200 via a picture archiving and communication system (PACS). The communicator 3200 may perform data communication according to digital imaging and communications in medicine (DICOM).

The communicator 3200 may transmit data relating to diagnosis of the object, for example, ultrasound images, ultrasound data, Doppler data, etc., of the object 10, via the network 30, and may receive medical images captured by other medical apparatuses such as a CT, an MRI, an X-ray, etc. The communicator 3200 may receive information about a medical history or treatment schedule of a patient from the server 4000, to be used in the diagnosis of the object 10.

The communicator 3200 may transmit first ultrasound information about the ultrasound image to the first device 1000 and second ultrasound information about the ultrasound image to the second device 2000 according to the sharing levels that are set in advance.

The communicator 3200 may receive a message about the ultrasound image from the second device 2000. The message may include a voice message, a text message, or a video message. The communicator 3200 may transmit a user input to the second device 2000, and may receive a response message from the second device 2000.

According to an exemplary embodiment, the communicator 3200 may transmit a request for confirmation of the second ultrasound information to the second device 2000, and may receive a confirmation message of the second ultrasound information from the second device 2000.

The communicator 3200 may receive control information from the second device 2000. The control information may include at least one of a control command for selecting and displaying a different ultrasound image from a currently displayed image, a control command for expanding or reducing the ultrasound image, a control command for storing the ultrasound image, a control command for 3D rendering the ultrasound image, a control command for adding an annotation or a body marker, a control command for measuring a region of interest, and a control command for correcting analysis information of the ultrasound image; however, the exemplary embodiments are not limited thereto.

The communicator 3200 may request the server 4000 for authentication of the first device 1000 and the second device 2000, and if the authentication succeeds, the communicator 3200 may receive sharing level information of the first device 1000 and the second device 2000 from the server 4000.

The controller 3300 controls operations of the ultrasound apparatus 3000. That is, the controller 3300 may control the ultrasound image obtainer 3100, the communicator 3200, the user input unit 3400, the memory 3500, and the display 3600.

For example, the controller 3300 may identify the sharing level of each of the first and second devices 1000 and 2000 for sharing the ultrasound image. The controller 3300 may generate first ultrasound information corresponding to a first sharing level of the first device 1000, and second ultrasound information corresponding to a second sharing level of the second device 2000.

When a touch input that touches the annotation displayed on the ultrasound image for a predetermined time period or longer is sensed, the controller 3300 may enable the touched annotation to move. The controller 3300 may select a region of interest from the ultrasound image, and may indicate an identification mark on the region of interest.

The controller 3300 may execute a control command corresponding to the control information transmitted from the second device 2000.

The user input unit 3400 is a unit used by the user (for example, the technician) to input data for controlling the ultrasound apparatus 3000. For example, the user input unit 3400 may be a keypad, a dome switch, a touch pad (a contact capacitance type, a pressure resistive type, an infrared sensing type, a surface ultrasound transfer type, an integral tension measurement type, a piezo effect type, etc.), a trackball, or a jog switch; however, the exemplary embodiments are not limited thereto. That is, the user input unit 3400 may further include an electrocardiogram (ECG) measuring module, a respiratory sensor module, a voice recognition sensor, a gesture recognition sensor, a fingerprint recognition sensor, an iris recognition sensor, a depth sensor, a distance sensor, etc.

The user input unit 3400 of an exemplary embodiment may detect a proximity touch, as well as a real-touch. The user input unit 3400 may sense a touch input on the ultrasound image (for example, a touch-and-hold, a tap, a double tap, or a flicking operation). The user input unit 3400 may sense a drag input from a point where a touch input is sensed. The user input unit 3400 may sense a multiple touch input (for example, a pinch operation) on at least two or more points included in the ultrasound image.

For example, the user input unit 3400 may receive a selection of at least one annotation included in the annotation list displayed on the screen. The user input unit 3400 may receive a drag and drop input that involves dragging the selected annotation to the region where the ultrasound image is displayed and dropping the annotation, and may sense a drag input of the user onto the annotation displayed on the ultrasound image.

The user input unit 3400 may receive a user input about the ultrasound image through the chatting window.

The memory 3500 may store programs for processing and controlling the controller 3300, and may store input/output data (for example, the annotation list set in advance, the ultrasound images, the patient information, probe information, body markers, etc.).

The memory 3500 may include a storage medium including at least one of a flash memory, a hard disk, a micro multimedia card, a card-type memory (e.g., a security digital (SD) or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The ultrasound apparatus 3000 may operate web storage or a cloud server for performing the storing function of the memory 3500 on the Internet.

The display 3600 displays and outputs the information processed by the ultrasound apparatus 3000. For example, the display 3600 displays the ultrasound images, or may display a user interface (UI) or GUI related to a control panel. The display 3600 may display a list of devices that may communicate with the ultrasound apparatus 3000, an annotation list about the plurality of annotations that are set in advance, and an activated annotation list about the annotations displayed on the screen.

According to an exemplary embodiment, the display 3600 may display an annotation selected from the annotation list on the ultrasound image. For example, the display 3600 may display the selected annotation based on the drag and drop input about the annotation included in the annotation list.

The display 3600 may move the displayed location of the annotation according to the drag input of the user. The display 3600 may display an activated annotation list about at least one annotation added to the ultrasound image on a predetermined region of the screen.

The display 3600 of an exemplary embodiment may display a message received from the second device 2000 and may provide a chatting window for communicating with the second device 2000 on the screen thereof.

If a display panel and a touchpad are layered to form a touchscreen, the display 3600 may be used as an input device as well as an output device. The display 3600 may include at least one of a liquid crystal display (LCD), a thin film transistor-liquid crystal display (TFT-LCD), an organic light-emitting diode (OLED), a flexible display, a 3D display, and an electrophoretic display. According to the form of the ultrasound apparatus 3000, the ultrasound apparatus 3000 may include two or more displays 3600.

Figure 23:
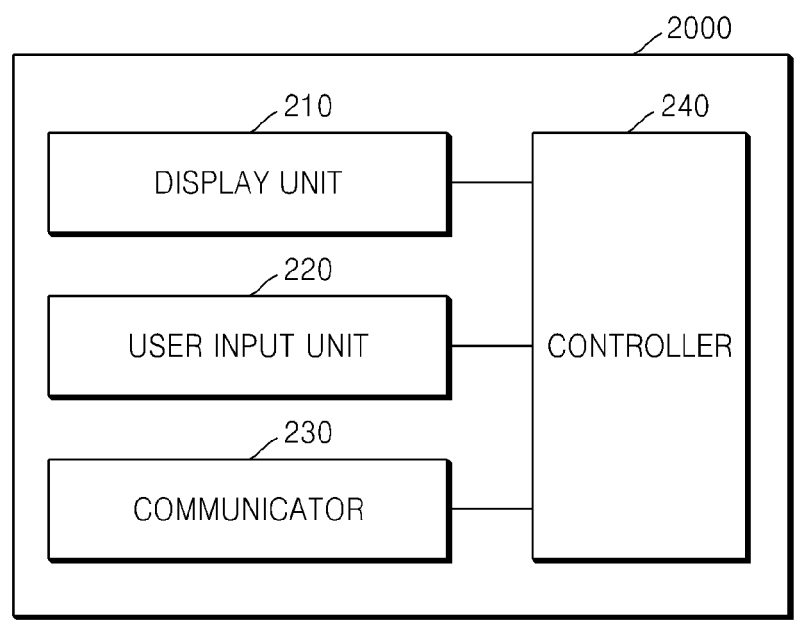
FIG. 23 is a block diagram showing a device according to an exemplary embodiment.

FIG. 23 is a block diagram showing a second device 2000 according to an exemplary embodiment.

As shown in FIG. 23, the second device 2000 of an exemplary embodiment may include a display 210, a user input unit 220, a communicator 230, and a controller 240. However, not all the components shown in FIG. 23 are essential elements. That is, the second device 2000 may include more or less components than those of FIG. 23.

The second device 2000 may include a mobile terminal and/or a stationary terminal. Examples of the mobile terminal may include a laptop computer, a personal digital assistant (PDA), a tablet PC, etc.

Hereinafter, the above components will be described.

The display 210 displays and outputs information processed by the second device 2000. For example, the display 210 may display an ultrasound image list including at least one ultrasound image acquired by at least one ultrasound apparatus 3000 on a first region of the screen, and may display an ultrasound image selected from the ultrasound image list on a second region of the screen. The ultrasound image list of an exemplary embodiment may include real-time ultrasound images transmitted from at least one ultrasound apparatus and ultrasound images stored in advance. According to another exemplary embodiment, the ultrasound image list may include real-time ultrasound images transmitted from the ultrasound apparatus 3000 only, or ultrasound images stored in advance.

The display 210 may display at least one of analysis information of the technician about the ultrasound image, measurement information with respect to the ultrasound image, and patient information, in addition to the ultrasound image, according to a sharing level of the second device 2000.

The display 210 may indicate a pointer of the ultrasound apparatus 3000 and a pointer of the second device 2000, and may provide a chatting window for communicating with the ultrasound apparatus 3000 on a third region of the screen. The display 210 may display a GUI for receiving a confirmation input about the ultrasound image from the medical expert (for example, a doctor).

The user input unit 220 is a unit for inputting data for controlling the second device 2000 from the medical expert (for example, the doctor). For example, the user input unit 220 may be a keypad, a dome switch, a touch pad (a contact capacitance type, a pressure resistive type, an infrared sensing type, a surface ultrasound transfer type, an integral tension measurement type, a piezo effect type, etc.), a trackball, or a jog switch; however, the exemplary embodiments are not limited thereto. In particular, if a touch pad is layered with a display panel, this is referred to as a touch screen.

The user input unit 220 of an exemplary embodiment may detect a proximity touch, as well as a real-touch. The user input unit 220 may sense a touch input on the ultrasound image (for example, a touch-and-hold, a tap, a double tap, or a flicking operation). The user input unit 220 may sense a drag input from a point where a touch input is sensed. The user input unit 220 may sense a multiple touch input (for example, a pinch operation) on at least two or more points included in the ultrasound image.

According to an exemplary embodiment, the user input unit 220 may receive a selection of an ultrasound image from the ultrasound image list. The user input unit 220 may receive an input of the user about the ultrasound image through the chatting window, and may receive a confirmation input about the ultrasound image through the GUI for receiving the confirmation input.

The user input unit 220 may receive a description by the medical expert about the ultrasound image. The description by the medical expert may include representing a region of interest (for example, a tumor, an embryo, a head of the embryo, a hand of the embryo, etc.), a description about the region of interest, an analysis result of the measurement value (for example, head girth, the number of fingers of an embryo, etc.), or existence of lesions; however, the exemplary embodiments are not limited thereto.

The communicator 230 may include one or more components enabling communications between the ultrasound apparatus 3000 and the first device 1000, the ultrasound apparatus 3000 and the second device 2000, and the ultrasound apparatus 3000 and the server 4000. For example, the communicator 230 may include a short distance communication module, a mobile communication module, a wired internet module, a wireless internet module, etc.

The short distance communication module refers to a module for short distance communication. As a short distance communication technology, WLAN (e.g., Wi-Fi), Bluetooth, BLE, UWB, ZigBee, NFC, WFD, IrDA, etc. may be used.

The mobile communication module transmits and receives wireless signals to and from at least one of a base station, an external device, and a server on a mobile communication network. The wireless internet module is a module for accessing wireless internet, and may be built into or provided outside the second device 2000. The wired internet module is a module for accessing wired internet.

The communicator 230 may communicate with the ultrasound apparatus 3000 that acquires the ultrasound image selected by the medical expert (for example, the doctor). For example, the communicator 230 may transmit an input about the ultrasound image to the ultrasound apparatus 3000. The communicator 230 may receive a request for confirmation about the selected ultrasound image from the ultrasound apparatus 3000, and may transmit the confirmation information about the selected ultrasound image to the ultrasound apparatus 3000.

The communicator 230 may transmit control information for controlling the ultrasound apparatus 3000 to the ultrasound apparatus 3000. For example, the communicator 230 may transmit to the ultrasound apparatus 3000 at least one of a control command for selecting and displaying another ultrasound image, a control command for expanding or reducing the ultrasound image, a control command for storing the ultrasound image, a control command for 3D rendering the ultrasound image, a control command for adding an annotation or a body marker, a control command for measuring a region of interest, and a control command for correcting analysis information of the ultrasound image. The communicator 230 may transmit the description by the medical expert to the first device 1000.

The controller 240 controls overall operations of the second device 2000. That is, the controller 240 may control the display 210, the user input unit 220, and the communicator 230.

According to an exemplary embodiment, the controller 240 may indicate an identification mark on the real-time ultrasound image for distinguishing the real-time ultrasound image from the ultrasound images that are stored in advance.

The above-described exemplary embodiments may be implemented with at least one processor and include a computer-readable medium including program instructions for executing various operations realized by a computer. The computer-readable medium may include program instructions, a data file, and a data structure, separately or cooperatively. The program instructions and the media may be specially designed and constructed for the purposes of the exemplary embodiments, or may be of a kind known to one of ordinary skill in the art of computer software arts. Examples of the computer-readable media include magnetic media (e.g., hard disks, floppy disks, and magnetic tapes), optical media (e.g., CD-ROMs or DVD), magneto-optical media (e.g., floptical disks), and hardware devices (e.g., ROMs, RAMs, or flash memories, etc.) that are specially configured to store and perform program instructions. The media may also be transmission media such as optical or metallic lines, wave guides, etc. specifying the program instructions, data structures, etc. Examples of the program instructions include both machine code, such as that produced by a compiler, and files containing high-level languages codes that may be executed by the computer using an interpreter.

Figure 24:
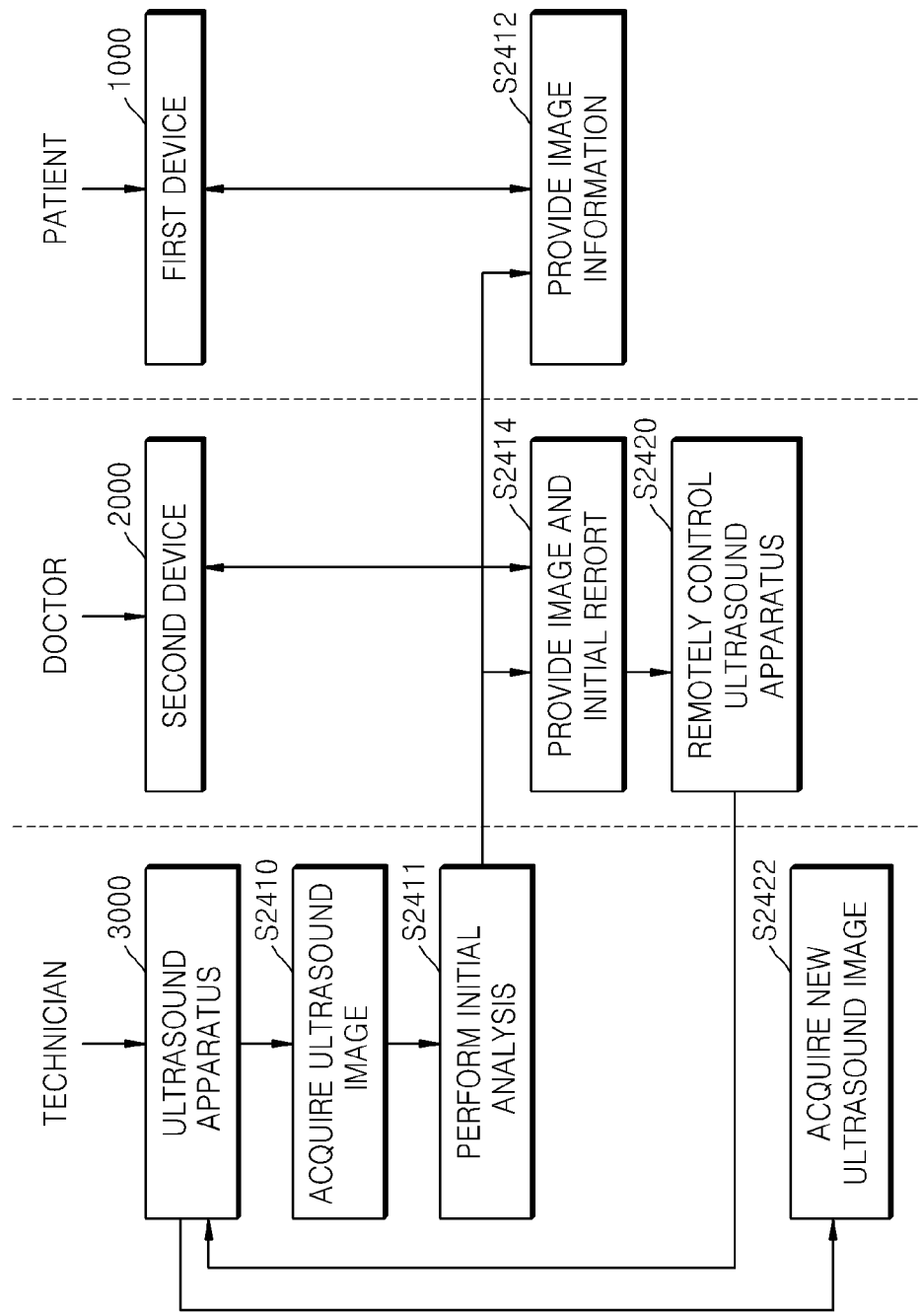
FIG. 24 illustrates a communication method according to an exemplary embodiment.

According to the exemplary embodiments, the ultrasound apparatus may transmit appropriate ultrasound information to a receiving device according to a sharing authority of the receiving device (for example, the patient device and the medical expert device). The sharing authority level may be determined so that excessive exposure of the ultrasound information may be prevented. With reference to FIG. 24, the technician of the ultrasound apparatus 3000 may acquire the ultrasound image of the patient, in operation S2410, and may perform initial analysis and processing of the ultrasound image, in operation S2411. The ultrasound apparatus 3000 may provide the second device 1000 with the ultrasound information that the patient may easily comprehend, in operation S2412. For example, the patient may be provided with a display of the ultrasound image in which the features of interest are signified by color and annotated and/or explained by text. In operation S2414, the ultrasound apparatus 3000 may provide the second device 2000 of the medical expert (for example, the doctor) with more detailed information. The doctor may be additionally provided with detailed medical history of the patient, report of the technician performing the imaging procedure of the patient, etc. The operations S2412 and S2414 may be one operation filtered by the different sharing authority levels assigned to the first device 1000 and the second device 2000. The exchange of the above information may be performed in real time or substantially contemporaneously with the imaging procedure performed by the technician who operates the ultrasound.

Since the user of the ultrasound apparatus may communicate with the medical expert about the ultrasound images in real-time, the doctor may provide an expeditious feedback and may direct appropriate operations, for example, during the imaging procedure or while transferring a patient in an emergency to a hospital, i.e., the number of ultrasound images taken and the time for diagnosis and imaging procedure may be minimized. For example, the doctor located in a remote location may check the image and remotely direct the ultrasound apparatus to re-take the image, change the scan direction, take a different image, perform calibration, change imaging parameters, etc. (operations S2420 and S2422). For example, the doctor may control the scan direction and movement of the ultrasound probe, by operating the remote controller provided via the doctor's device. The remote location may be a location disposed in a different or isolated geographic locality as that of the ultrasound apparatus and the patient.

Further, with an exemplary ultrasound apparatus, the patients may better comprehend the images and may diagnose themselves, i.e., a self-diagnosis is possible.

In the above description, the method of sharing information about ultrasound images between the ultrasound apparatus 3000 and at least one external device according to a sharing level is described as an example; however, exemplary embodiments are not limited thereto. For example, other medical imaging apparatuses in addition to the ultrasound apparatus 3000 may share information about medical images with the external device according to a sharing level of the external device. A method of sharing information about medical images by the medical imaging apparatus with at least one external device will be described with reference to FIG. 25.

Figure 25:
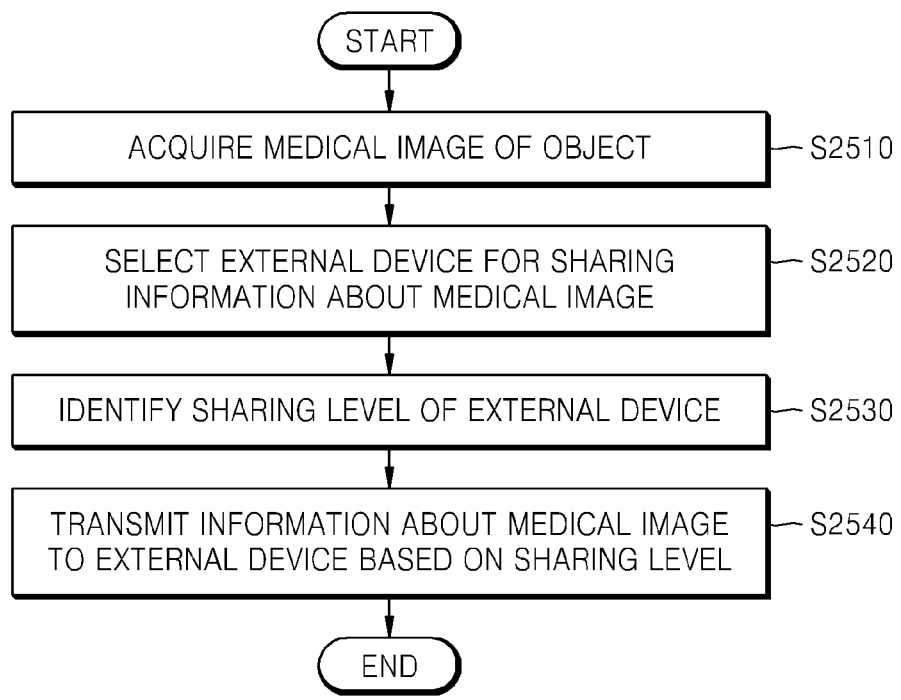
FIG. 25 is a flowchart illustrating an information sharing method of a medical imaging apparatus according to an exemplary embodiment.

FIG. 25 is a flowchart illustrating an information sharing method of a medical imaging apparatus according to an exemplary embodiment.

In operation S2510, the medical imaging apparatus may acquire a medical image of an object. According to the present exemplary embodiment, the medical imaging apparatus may directly generate the medical image or may receive the medical image from outside.

In the present specification, the medical imaging apparatus may include a magnetic resonant imaging (MRI) apparatus, a computerized tomography (CT) apparatus, an X-ray imaging apparatus, an angiography apparatus, and the like; however, exemplary embodiments are not limited thereto.

An MRI apparatus is an apparatus for acquiring a sectional image of a part of an object by expressing, in a contrast comparison, a strength of a MR signal with respect to a radio frequency (RF) signal generated in a magnetic field having a specific strength.

Since a CT apparatus is capable of providing a cross-sectional image of a object, the CT apparatus may express an inner structure (e.g., an organ such as a kidney, a lung, etc.) of the object without an overlap therebetween. The CT apparatus may obtain a plurality of pieces of image data with a thickness not more than 2 mm for several tens to several hundreds of times per second and then may process the plurality of pieces of image data, so that the CT apparatus may provide a relatively accurate a cross-sectional image of the object.

An X-ray imaging apparatus is an apparatus for imaging internal organic structure of an object by transmitting an X-ray through the object. An angiography apparatus is an apparatus for imaging blood vessels (arteries and veins), in which a contrast medium is injected through a thin tube having a diameter of about 2 mm, called as a catheter, by transmitting an X-ray.

According to the present exemplary embodiment, the medical imaging apparatus may be realized in various formats. For example, the medical imaging apparatus recited in the present specification may be configured as a mobile terminal type, as well as a stationary terminal type. Examples of the mobile terminal may include smartphones, laptop computers, personal digital assistants (PDAs), tablet PCs, and the like.

According to the exemplary embodiments, the medical image may include an MRI, a CT image, an ultrasound image, and an X-ray image; however, the exemplary embodiments are not limited thereto. Also, the medical image may be a two-dimensional image, a three-dimensional image, or a four-dimensional image; however, the exemplary embodiments are not limited thereto. Hereinafter, the medical image is assumed as a two-dimensional X-ray image for the convenience of description.

In operation S2520, the medical imaging apparatus may select an external device, with which information about a medical image will be shared.

According to the present exemplary embodiment, the medical imaging apparatus may select a first device 1000 and a second device 2000 that are connected to the medical imaging apparatus based on system settings.

According to another exemplary embodiment, the medical imaging apparatus may select the first device 1000 and the second device 2000 based on a user input. For example, the medical imaging apparatus may provide a device list including identification information of devices that may communicate with the medical imaging apparatus on a screen. The medical imaging apparatus may receive a user input for the first device 1000 and the second device 2000 in the device list. The user of the medical imaging apparatus according to the present exemplary embodiment may be an ultrasound technician, a radiological technologist, an ambulance attendant, or an ordinary person; however, the exemplary embodiments are not limited thereto.

Information about the medical image may include at least one piece of information from among information about the medical image itself, annotation information for describing all or some of the medical image, identification mark information for identifying a region of interest in the medical image, analyzing information generated by the radiological technologist or the ultrasound technician, information about the object, and measuring information; however, the exemplary embodiments are not limited thereto.

In operation S2530, the medical imaging apparatus may identify a sharing level of the selected external device. The sharing level may include information representing authority of a user of the external device for checking the information about the medical image. The sharing level may be set in advance by information sharing system or a user.

For example, the medical imaging apparatus may identify information about a first sharing level corresponding to identification information of the first device 1000 and/or a second sharing level corresponding to the identification information of the second device 2000.

According to the present exemplary embodiment, the medical imaging apparatus may receive information about the first sharing level and/or information about the second sharing level from a server 4000. Also, according to another exemplary embodiment, the medical imaging apparatus may read the information about the first sharing level and/or the information about the second sharing level stored in the memory.

According to the exemplary embodiment, the first sharing level of the first device 1000 and the second sharing level of the second device 2000 may be different from each other. For example, if the first device 1000 is an object device and the second device 2000 is a medical expert device, the sharing level of the first device 1000, that is, the object device, may be lower than the sharing level of the second device 2000, that is, the medical expert device. Relative low sharing level denotes that a type and/or amount of information that may be shared is relatively small.

In operation S2540, the medical imaging apparatus may transmit information about the medical image to the external device based on the sharing level.

According to the exemplary embodiment, the medical imaging apparatus may transmit first medical image information corresponding to the first sharing level to the first device 1000, or may transmit second medical image information corresponding to the second sharing level to the second device 2000. Here, according to the present exemplary embodiment, the medical imaging apparatus may generate the first medical image information and the second medical image information.

The medical imaging apparatus may generate the first medical image information corresponding to the first sharing level of the first device 1000. For example, if the first device 1000 is the object device, the medical imaging apparatus may generate the first medical image information including the medical image, annotation for describing the medical image, an identification mark on the region of interest, and measuring information according to the first sharing level of the object device.

The medical imaging apparatus may generate the second medical image information corresponding to the second sharing level of the second device 2000. For example, if the second device 2000 is the medical expert device, the medical imaging apparatus may generate the second medical image information including the medical image, measuring information of the medical image, analyzing information of the medical image by the radiological technologist, and object information according to the second sharing level of the medical expert device.

Therefore, according to the exemplary embodiment, in a case where the first device 1000 is the object device and the second device 2000 is the medical expert device, the medical imaging apparatus may share the first medical image information including the annotation for describing the medical image, the identification mark on the region of interest, and the measuring information with the first device 1000, and may share the second medical image information including the medical image, the measuring information of the medical image, the analyzing information of the medical image by the radiological technologist, and the object information with the second device 2000.

In addition, according to the exemplary embodiment, the medical imaging apparatus encodes the first medical image information and/or the second medical image information with an encoding code that is negotiated in advance or set in advance for security of the first medical image information and/or the second medical image information, and transmits the encoded first medical image information and/or second medical image information to the first device 1000 or the second device 2000.

Hereinafter, processes of sharing information about the medical image (for example, an X-ray image) by the medical imaging apparatus (for example, an X-ray imaging apparatus) with at least one external device according to the sharing level will be described below with reference to FIGS. 26 through 28.

Figure 26:
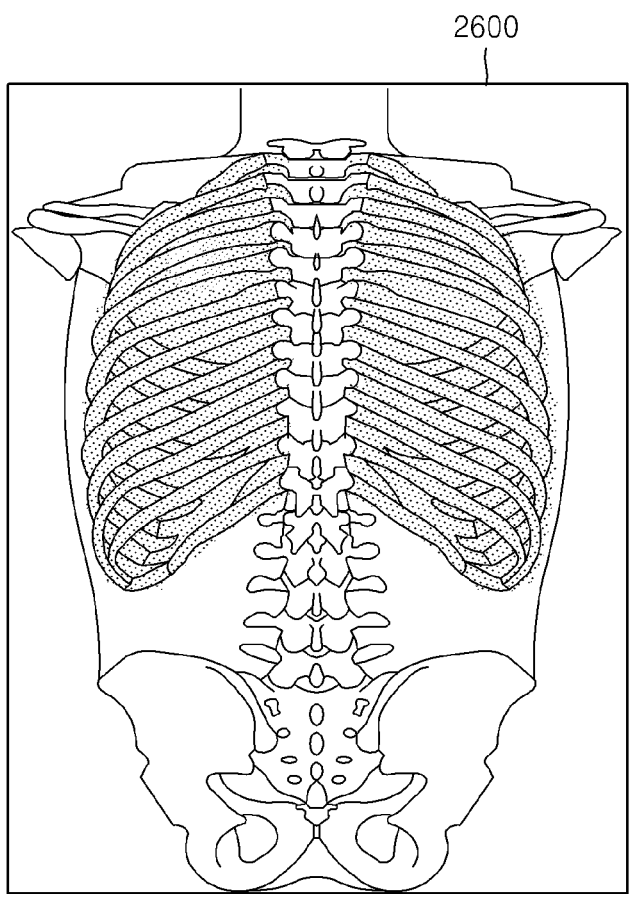
FIG. 26 is a diagram showing an X-ray image obtained by an X-ray imaging apparatus according to an exemplary embodiment.

FIG. 26 is a diagram showing an X-ray image acquired by an X-ray imaging apparatus according to an exemplary embodiment.

As shown in FIG. 26, the X-ray imaging apparatus may acquire an X-ray chest image 2600 of an object by using the X-ray. In this case, the X-ray photographing apparatus may select an external device with which information about the X-ray chest image 2600 will be shared. For example, the X-ray imaging apparatus may select an object device for describing the X-ray chest image 2600 to the object.

The X-ray imaging apparatus may identify a sharing level of the selected object device. In addition, the X-ray imaging apparatus may generate information about the X-ray chest image 2600 that will be shared with the object device according to the sharing level.

For example, if the sharing level of the object device is a first level, the X-ray imaging apparatus generates a bone suppression image that is obtained by deleting bones from the X-ray chest image 2600, and marks a region of interest on the bone suppression image. This will be described with reference to FIG. 27.

Figure 27:
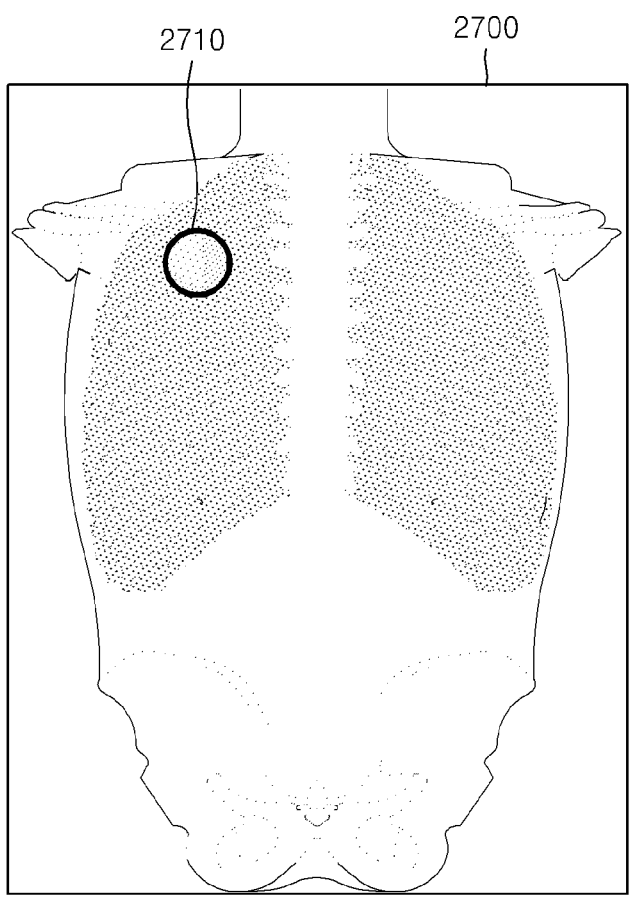
FIG. 27 is a diagram showing a Bone suppression image, in which a region of interest is marked, according to an exemplary embodiment.

As shown in FIG. 27, the X-ray imaging apparatus may generate a bone suppression image 2700 by deleting bones from the X-ray chest image 2600 so that the object may clearly see lesion. In addition, the X-ray imaging apparatus selects a region that is suspected to have nodule on the bone suppression image 2700 as a region of interest 2710, and displays a mark for the region of interest 2710. Here, the X-ray imaging apparatus may select the region of interest 2710 automatically or based on a user input. In FIG. 27, the region of interest 2710 is marked by a circle; however, the exemplary embodiments are not limited thereto.

The X-ray imaging apparatus may transmit information about the bone suppression image 2700 and information about the region of interest 2710 to the object device according to the sharing level of the object device (for example, the first level). Here, the object device may display the bone suppression image 2700 including the region of interest 2710 on a screen.

In addition, if the sharing level of the object device is a second level, the X-ray imaging apparatus may additionally generate information about annotation for describing the region of interest 2710 (for example, text, font, and display location information). This will be described with reference to FIG. 28.

Figure 28:
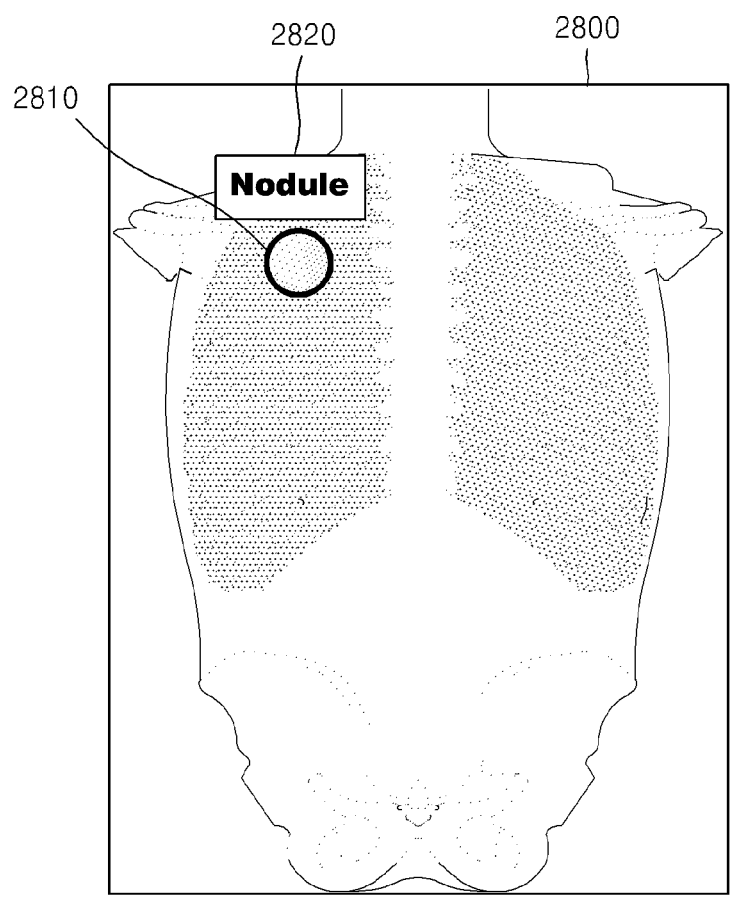
FIG. 28 is a diagram showing an X-ray image including an annotation according to an exemplary embodiment.

As shown in FIG. 28, the X-ray imaging apparatus may generate a bone suppression image 2800 by deleting bones from the X-ray chest image 2600 so that the object may clearly see the lesion. In addition, the X-ray imaging apparatus selects a part suspected to be a nodule as a region of interest 2810 on the bone suppression image 2800, and may generate an annotation 2820 about the region of interest 2810. The X-ray imaging apparatus may generate the annotation 2820 automatically or based on a user input.

The X-ray imaging apparatus may transmit information about the bone suppression image 2800, information about the region of interest 2810, and information about the annotation 2820 to the object device according to the sharing level of the object device (for example, the second level). The object device may display the bone suppression image 2800 including the region of interest 2810 and the annotation 2820 on a screen.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An ultrasound apparatus comprising:
a probe configured to acquire an echo signal from an object;
a communicator configured to communicate with an external device comprising a touch screen;
a display; and
at least one processor configured to:
generate a first ultrasound image using ultrasound data corresponding to the echo signal obtained by the probe;
display the first ultrasound image on the display;
control the communicator to transmit the first ultrasound image to the external device so that the first ultrasound image, which is the same first ultrasound image as displayed on the display of the ultrasound apparatus, is displayed on the touch screen of the external device;
receive, from the external device, a control command generated in response to a touch input which is provided by a user of the external device on the touch screen of the external device and is related to the first ultrasound image displayed on the touch screen of the external device, the control command received from the external device comprising adding a body marker including a first figure representing the object and a second figure representing a location of the probe contacting the object;
in response to the control command received from the external device, obtain a second ultrasound image by adding the body marker to the first ultrasound image;
display the second ultrasound image including the body marker instead of the first ultrasound image on the display; and
control the communicator to transmit the second ultrasound image to the external device so that the second ultrasound image, which is the same second ultrasound image as displayed on the display of the ultrasound apparatus, is displayed on the touch screen of the external device,
wherein the second ultrasound image obtained according to the control command received from the external device is displayed simultaneously on the display of the ultrasound apparatus and the touch screen of the external device.

2. The ultrasound apparatus of claim 1, wherein the control command comprises at least one from among a control command for expanding or reducing the first ultrasound image, a control command for performing a three-dimensional (3D) rendering of the first ultrasound image, a control command for adding an annotation, a control command for measuring a region of interest, and a control command for correcting analysis information about the first ultrasound image.

3. The ultrasound apparatus of claim 1, wherein the processor is further configured to:
display a GUI;
receive a user input for selecting at least one annotation for describing the first ultrasound image and a region of interest in the first ultrasound image by using the GUI;

display or save the at least one annotation for describing the first ultrasound image, an identification mark on the region of interest, and measurement information for the region of interest; and control the communicator to transmit ultrasound information to the external device, the ultrasound information comprising at least one from among the at least one annotation for describing the first ultrasound image, the identification mark on the region of interest, and the measurement information for the region of interest.

4. The ultrasound apparatus of claim 1, wherein the processor is further configured to:
identify a sharing level of the external device, which designates an authority of the user of the external device to review information about the first ultrasound image; and
control the communicator to transmit the information about the first ultrasound image to the external device, according to the sharing level.

5. The ultrasound apparatus of claim 1, wherein the processor is further configured to:
control the communicator to transmit a request for confirmation of the first ultrasound image to the external device and receive a confirmation message of the first ultrasound image from the external device; and
represent that the first ultrasound image displayed on the display is confirmed by the external device.

6. The ultrasound apparatus of claim 1, wherein the processor is further configured to encode the first ultrasound image to transmit the first ultrasound image to the external device, and wherein the communicator is configured to transmit the first ultrasound image via at least one from among Wi-Fi Direct (WFD), Wi-Fi, Bluetooth, Ultra-Wideband (UWB), and IEEE 1394.

7. The ultrasound apparatus of claim 1, wherein the at least one processor is further configured to:
receive a second touch input which is provided by a user of the ultrasound apparatus on the display of the ultrasound apparatus;
in response to the receiving of the second touch input, control the communicator to transmit a confirmation request associated with the second ultrasound image to the external device;
receive a confirmation message from the external device; and
in response to the receiving of the confirmation message, display a confirmation notification on the display of the ultrasound apparatus.

8. The ultrasound apparatus of claim 1, wherein the communicator is configured to transmit the first ultrasound image in real-time,
wherein an additional control command is generated in response to a pinch input provided by the user of the external device on the real-time first ultrasound image displayed on the external device, and
wherein the processor is configured to:
control the communicator to receive the additional control command;
generate a real-time second ultrasound image by expanding or reducing the real-time first ultrasound image; and
control the communicator to transmit the real-time second ultrasound image to the external device.

9. The ultrasound apparatus of claim 8, wherein the control command is for expanding the real-time first ultrasound image according to a distance between fingers of the user of the external device, when the user of the external device touches the touch screen of the external device with the fingers and increases the distance between the fingers, or for reducing the real-time first ultrasound image according to the distance between the fingers of the user of the external device, when the user of the external device touches the touch screen of the external device with the fingers and reduces the distance between the fingers.

10. A method of sharing information with an external device by an ultrasound apparatus, the method comprising:
acquiring, by the ultrasound apparatus, ultrasound data from an object;
generating, by the ultrasound apparatus, a first ultrasound image using the ultrasound data;
displaying the first ultrasound image on a display of the ultrasound apparatus;
transmitting, by the ultrasound apparatus, the first ultrasound image to the external device so that the first ultrasound image, which is the same first ultrasound image as displayed on the display of the ultrasound apparatus, is displayed on a touch screen of the external device;
receiving, by the ultrasound apparatus from the external device, a control command generated in response to a touch input which is provided by a user of the external device on the touch screen of the external device and is related to the first ultrasound image displayed on the touch screen of the external device, the control command received from the external device comprising adding a body marker including a first figure representing the object and a second figure representing a location of the probe contacting the object;
in response to the receiving the control command from the external device, obtain a second ultrasound image by adding the body marker to the first ultrasound image;
displaying the second ultrasound image including the body marker instead of the first ultrasound image on the display;
transmitting the second ultrasound image to the external device so that the second ultrasound image, which is the same second ultrasound image as displayed on the display of the ultrasound apparatus, is displayed on the touch screen of the external device,
wherein the second ultrasound image obtained according to the control command received from the external device is displayed simultaneously on the display of the ultrasound apparatus and the touch screen of the external device.

11. An external device communicating with an ultrasound apparatus, the external device comprising:
a communicator configured to communicate with the ultrasound apparatus comprising a display;
a touch screen; and
a processor configured to:
receive, from the ultrasound apparatus via the communicator, a first ultrasound image which is generated by the ultrasound apparatus using ultrasound data obtained by the ultrasound apparatus and is displayed on the display of the ultrasound apparatus;
display the first ultrasound image on the touch screen, wherein the first ultrasound image is the same first ultrasound image as displayed on the display of the ultrasound apparatus;
receive a touch input which is provided via the touch screen by a user of the external device and related to the first ultrasound image displayed on the touch screen;
generate a control command in response to the receiving the touch input of the user of the external device, the control command comprising adding a body marker including a first figure representing the object and a second figure representing a location of the probe contacting the object;
control the communicator to transmit the control command to the ultrasound apparatus;
control the communicator to receive, from the ultrasound apparatus, a second ultrasound image, which is obtained by the ultrasound apparatus in response to the control command received from the external device by adding the body marker to the first ultrasound image, and is displayed on the display of the ultrasound apparatus; and
display the second ultrasound image, which is the same second ultrasound image as displayed on the display of the ultrasound apparatus, on the touch screen,
wherein the second ultrasound image including the body marker is displayed simultaneously on the display of the ultrasound apparatus and the touch screen of the external device.

12. The external device of claim 11, wherein the control command comprises at least one from among a control command for expanding or reducing the first ultrasound image, a control command for performing a three-dimensional (3D) rendering of the first ultrasound image, a control command for adding an annotation, a control command for measuring a region of interest, and a control command for correcting analysis information about the first ultrasound image.

13. The external device of claim 11, wherein the processor is further configured to:
control the communicator to receive a request for confirmation of the first ultrasound image from the ultrasound apparatus and transmit a confirmation message of the first ultrasound image to the ultrasound apparatus.

14. The external device of claim 11, wherein the processor is further configured to:
display an ultrasound image list on the touch screen;
receive a selection of the first ultrasound image from the ultrasound image list via the touch screen; and
control the communicator to communicate with the ultrasound apparatus that acquires the first ultrasound image.

15. The external device of claim 11, wherein the processor is further configured to:
control the communicator to receive ultrasound information comprising at least one from among an annotation for describing the first ultrasound image, an identification mark on a region of interest, and measurement information for the region of interest from the ultrasound apparatus; and
display the ultrasound information on the touch screen.

16. The external device of claim 11, wherein the processor is further configured to receive information about the first ultrasound image from the ultrasound apparatus according to a sharing level of the external device, which designates an authority of the user of the external device to review the information about the first ultrasound image.

17. The external device of claim 11, wherein the communicator is configured to receive the first ultrasound image in real-time, and
wherein the processor is further configured to:
receive a pinch input on the real-time first ultrasound image; and
control the communicator to transmit an additional control command for expanding or reducing the real-time first ultrasound image in response to the pinch input to the ultrasound apparatus, the transmitted additional control command being used to generate a real-time second ultrasound image by expanding or reducing the real-time first ultrasound image by the ultrasound apparatus.

18. The external device of claim 17, wherein the control command is for expanding the real-time first ultrasound image according to a distance between fingers of the user of the external device, when the user of the external device touches the touch screen with the fingers and increases the distance between the fingers, or for reducing the real-time first ultrasound image according to the distance between the fingers of the user of the external device, when the user of the external device touches the touch screen with the fingers and reduces the distance between the fingers.

19. A method of communicating with an ultrasound apparatus by an external device, the method comprising:
receiving, from the ultrasound apparatus, a first ultrasound image which is generated by the ultrasound apparatus using ultrasound data obtained by the ultrasound apparatus and is displayed on a display of the ultrasound apparatus;
displaying the first ultrasound image on a touch screen of the external device, wherein the first ultrasound image is the same first ultrasound image as displayed on the display of the ultrasound apparatus;
receiving a touch input which is provided via the touch screen by a user of the external device and related to the first ultrasound image displayed on the touch screen;
generating a control command in response to the receiving the touch input of the user of the external device, the control command comprising adding a body marker including a first figure representing the object and a second figure representing a location of the probe contacting the object;
transmitting the control command to the ultrasound apparatus;
receiving, from the ultrasound apparatus, a second ultrasound image, which is obtained by the ultrasound apparatus in response to the control command received from the external device by adding the body marker to the first ultrasound image, and is displayed on the display of the ultrasound apparatus;
displaying the second ultrasound image, which is the same second ultrasound image as displayed on the display of the ultrasound apparatus, on the touch screen,
wherein the second ultrasound image including the body marker is displayed simultaneously on the display of the ultrasound apparatus and the touch screen of the external device.

20. A computer program product comprising a computer readable storage medium having a computer readable program stored therein, wherein the computer readable program, when executed on an ultrasound apparatus, causes the ultrasound apparatus to:
acquire an echo signal from an object using a probe;
generate a first ultrasound image using ultrasound data corresponding to the echo signal obtained by the probe;
display the first ultrasound image on a display of the ultrasound apparatus;
transmit the first ultrasound image to an external device so that the first ultrasound image, which is the same first ultrasound image as displayed on the display of the ultrasound apparatus, is displayed on a touch screen of the external device;

receive, from the external device, a control command generated in response to a touch input which is provided by a user of the external device on the touch screen of the external device and is related to the first ultrasound image displayed on the touch screen of the external device, the control command received from the external device comprising adding a body marker including a first figure representing the object and a second figure representing a location of the probe contacting the object;

in response to the control command received from the external device, obtain a second ultrasound image by adding the body marker to the first ultrasound image;

display the second ultrasound image on including the body marker instead of the first ultrasound image the display of the ultrasound apparatus; and transmit the second ultrasound image to the external device so that the second ultrasound image, which is the same second ultrasound image as displayed on the display of the ultrasound apparatus, is displayed on the touch screen of the external device, wherein the second ultrasound image obtained according to the control command received from the external device is displayed simultaneously on the display of the ultrasound apparatus and the touch screen of the external device.

* * * * *